(12) United States Patent
Jones

(10) Patent No.: US 7,767,145 B2
(45) Date of Patent: Aug. 3, 2010

(54) HIGH PRESSURE FOURIER TRANSFORM INFRARED CELL

(75) Inventor: William D. Jones, Phoenix, AZ (US)

(73) Assignee: Toyko Electron Limited, Tokyo (JP)

( * ) Notice: Subject to any disclaimer, the term of this patent is extended or adjusted under 35 U.S.C. 154(b) by 1062 days.

(21) Appl. No.: 11/091,976

(22) Filed: Mar. 28, 2005

(65) Prior Publication Data

US 2006/0216197 A1    Sep. 28, 2006

(51) Int. Cl.
*G01N 21/00* (2006.01)
(52) U.S. Cl. ........................................... 422/62
(58) Field of Classification Search ........... 422/62
See application file for complete search history.

(56) References Cited

U.S. PATENT DOCUMENTS

| | | | |
|---|---|---|---|
| 2,617,719 A | 11/1952 | Stewart | |
| 2,625,886 A | 1/1953 | Browne | |
| 2,873,597 A | 2/1959 | Fahringer | |
| 3,521,765 A | 7/1970 | Kauffman et al. | |
| 3,623,627 A | 11/1971 | Bolton | |
| 3,681,171 A | 8/1972 | Hojo et al. | |
| 3,744,660 A | 7/1973 | Gaines et al. | |
| 3,968,885 A | 7/1976 | Hassan et al. | |
| 4,029,517 A | 6/1977 | Rand | |
| 4,091,643 A | 5/1978 | Zucchini | |
| 4,145,161 A | 3/1979 | Skinner | |
| 4,244,557 A | 1/1981 | Polhede et al. | 251/167 |
| 4,245,154 A | 1/1981 | Uehara et al. | |
| 4,316,750 A | 2/1982 | Gengler | 134/18 |
| 4,341,592 A | 7/1982 | Shortes et al. | |
| 4,343,455 A | 8/1982 | Winkler | 251/58 |
| 4,355,937 A | 10/1982 | Mack et al. | |
| 4,367,140 A | 1/1983 | Wilson | |
| 4,391,511 A | 7/1983 | Akiyama et al. | |
| 4,406,596 A | 9/1983 | Budde | |
| 4,422,651 A | 12/1983 | Platts | |
| 4,426,388 A | 1/1984 | Johansson | |
| 4,474,199 A | 10/1984 | Blaudszun | |

(Continued)

FOREIGN PATENT DOCUMENTS

CN    1399790 A    2/2003

(Continued)

OTHER PUBLICATIONS

Hideaki Itakura et al., "Multi-Chamber Dry Etching System", Solid State Technology, Apr. 1982, pp. 209-214.

(Continued)

*Primary Examiner*—Walter D Griffin
*Assistant Examiner*—Bobby Ramdhanie
(74) *Attorney, Agent, or Firm*—Haverstock & Owens, LLP

(57) ABSTRACT

A monitoring system enables in-situ monitoring of a solution enclosed within a high-pressure, closed loop environment. The monitoring system includes a calcium fluoride disk that is substantially transparent to infrared light. A hole is configured through the disk and a solution passes through the hole. Solution passing through the hole is analyzed by directing infrared light through the disk and the solution currently moving through the hole in the disk. The light exiting the disk is collected and analyzed to determine the composition of the solution through which the light passed.

23 Claims, 7 Drawing Sheets

U.S. PATENT DOCUMENTS

| | | | |
|---|---|---|---|
| 4,522,788 A | 6/1985 | Sitek et al. | |
| 4,549,467 A | 10/1985 | Wilden et al. | |
| 4,574,184 A | 3/1986 | Wolf et al. | |
| 4,592,306 A | 6/1986 | Gallego | |
| 4,601,181 A | 7/1986 | Privat | |
| 4,618,769 A * | 10/1986 | Johnson et al. | 250/338.1 |
| 4,626,509 A | 12/1986 | Lyman | |
| 4,670,126 A | 6/1987 | Messer et al. | |
| 4,682,937 A | 7/1987 | Credle, Jr. | |
| 4,693,777 A | 9/1987 | Hazano et al. | |
| 4,749,440 A | 6/1988 | Blackwood et al. | |
| 4,778,356 A | 10/1988 | Hicks | |
| 4,788,043 A | 11/1988 | Kagiyama et al. | |
| 4,789,077 A | 12/1988 | Noe | |
| 4,823,976 A | 4/1989 | White, III et al. | |
| 4,825,808 A | 5/1989 | Takahashi et al. | |
| 4,827,867 A | 5/1989 | Takei et al. | |
| 4,838,476 A | 6/1989 | Rahn | |
| 4,865,061 A | 9/1989 | Fowler et al. | |
| 4,879,431 A | 11/1989 | Bertoncini | |
| 4,917,556 A | 4/1990 | Stark et al. | |
| 4,924,892 A | 5/1990 | Kiba et al. | |
| 4,951,601 A | 8/1990 | Maydan et al. | |
| 4,960,140 A | 10/1990 | Ishijima et al. | |
| 4,983,223 A | 1/1991 | Gessner | |
| 5,009,738 A | 4/1991 | Gruenwald et al. | |
| 5,011,542 A | 4/1991 | Weil | |
| 5,028,219 A | 7/1991 | Schuetz et al. | 417/423.4 |
| 5,044,871 A | 9/1991 | Davis et al. | |
| 5,062,770 A | 11/1991 | Story et al. | |
| 5,071,485 A | 12/1991 | Matthews et al. | |
| 5,105,556 A | 4/1992 | Kurokawa et al. | |
| 5,143,103 A | 9/1992 | Basso et al. | |
| 5,167,716 A | 12/1992 | Boitnott et al. | |
| 5,169,296 A | 12/1992 | Wilden | |
| 5,169,408 A | 12/1992 | Biggerstaff et al. | |
| 5,185,296 A | 2/1993 | Morita et al. | |
| 5,186,594 A | 2/1993 | Toshima et al. | |
| 5,186,718 A | 2/1993 | Tepman et al. | |
| 5,188,515 A | 2/1993 | Horn | |
| 5,190,373 A | 3/1993 | Dickson et al. | |
| 5,191,993 A | 3/1993 | Wanger et al. | |
| 5,193,560 A | 3/1993 | Tanaka et al. | |
| 5,195,878 A | 3/1993 | Sahiavo et al. | |
| 5,197,800 A | 3/1993 | Saidman et al. | 366/136 |
| 5,213,485 A | 5/1993 | Wilden | |
| 5,217,043 A | 6/1993 | Novakovic | |
| 5,221,019 A | 6/1993 | Pechacek | |
| 5,222,876 A | 6/1993 | Budde | |
| 5,224,504 A | 7/1993 | Thompson et al. | |
| 5,236,669 A | 8/1993 | Simmons et al. | |
| 5,237,824 A | 8/1993 | Pawliszyn | |
| 5,240,390 A | 8/1993 | Kvinge et al. | |
| 5,242,641 A | 9/1993 | Horner et al. | 264/104 |
| 5,243,821 A | 9/1993 | Schuck et al. | |
| 5,246,500 A | 9/1993 | Samata et al. | |
| 5,251,776 A | 10/1993 | Morgan, Jr. et al. | |
| 5,252,041 A | 10/1993 | Schumack | |
| 5,259,731 A | 11/1993 | Dhindsa et al. | |
| 5,267,455 A | 12/1993 | Dewees et al. | |
| 5,280,693 A | 1/1994 | Heudecker | |
| 5,285,352 A | 2/1994 | Pastore et al. | |
| 5,285,845 A | 2/1994 | Östbo | 165/168 |
| 5,288,333 A | 2/1994 | Tanaka et al. | |
| 5,306,350 A | 4/1994 | Hoy et al. | |
| 5,313,965 A | 5/1994 | Palen | |
| 5,314,574 A | 5/1994 | Takahashi | |
| 5,328,722 A | 7/1994 | Ghanayem et al. | |
| 5,331,986 A | 7/1994 | Lim et al. | 134/88 |
| 5,337,446 A | 8/1994 | Smith et al. | |
| 5,339,844 A | 8/1994 | Stanford, Jr. et al. | |
| 5,355,901 A | 10/1994 | Mielnik et al. | |
| 5,368,171 A | 11/1994 | Jackson | |
| 5,370,741 A | 12/1994 | Bergman | |
| 5,374,829 A | 12/1994 | Sakamoto et al. | |
| 5,377,705 A | 1/1995 | Smith, Jr. et al. | |
| 5,401,322 A | 3/1995 | Marshall | |
| 5,404,894 A | 4/1995 | Shiraiwa | |
| 5,412,958 A | 5/1995 | Iliff et al. | |
| 5,417,768 A | 5/1995 | Smith, Jr. et al. | |
| 5,433,334 A | 7/1995 | Reneau | |
| 5,434,107 A | 7/1995 | Paranjpe | 437/225 |
| 5,447,294 A | 9/1995 | Sakata et al. | |
| 5,474,410 A | 12/1995 | Ozawa et al. | |
| 5,494,526 A | 2/1996 | Paranjpe | |
| 5,503,176 A | 4/1996 | Dunmire et al. | |
| 5,505,219 A | 4/1996 | Lansberry et al. | |
| 5,509,431 A | 4/1996 | Smith, Jr. et al. | |
| 5,526,834 A | 6/1996 | Mielnik et al. | |
| 5,533,538 A | 7/1996 | Marshall | |
| 5,540,554 A | 7/1996 | Masuzawa | |
| 5,571,330 A | 11/1996 | Kyogoku | |
| 5,589,224 A | 12/1996 | Tepman et al. | |
| 5,621,982 A | 4/1997 | Yamashita et al. | |
| 5,629,918 A | 5/1997 | Ho et al. | |
| 5,643,368 A | 7/1997 | Nakashima | |
| 5,644,855 A | 7/1997 | McDermott et al. | |
| 5,649,809 A | 7/1997 | Stapelfeldt | |
| 5,656,097 A | 8/1997 | Olesen et al. | |
| 5,669,251 A | 9/1997 | Townsend et al. | |
| 5,672,204 A | 9/1997 | Habuka | |
| 5,702,228 A | 12/1997 | Tamai et al. | |
| 5,706,319 A | 1/1998 | Holtz | |
| 5,746,008 A | 5/1998 | Yamashita et al. | |
| 5,769,588 A | 6/1998 | Toshima et al. | |
| 5,772,783 A | 6/1998 | Stucker | |
| 5,797,719 A * | 8/1998 | James et al. | 417/46 |
| 5,798,126 A | 8/1998 | Fijikawa et al. | |
| 5,817,178 A | 10/1998 | Mita et al. | |
| 5,850,747 A | 12/1998 | Roberts et al. | |
| 5,858,107 A | 1/1999 | Chao et al. | |
| 5,865,602 A | 2/1999 | Nozari | |
| 5,879,459 A | 3/1999 | Gadgil et al. | |
| 5,881,577 A | 3/1999 | Sauer et al. | |
| 5,882,165 A | 3/1999 | Maydan et al. | |
| 5,882,182 A | 3/1999 | Kato et al. | 417/366 |
| 5,888,050 A | 3/1999 | Fitzgerald et al. | |
| 5,898,727 A | 4/1999 | Fujikawa et al. | |
| 5,900,107 A | 5/1999 | Murphy et al. | |
| 5,904,737 A | 5/1999 | Preston et al. | |
| 5,906,866 A | 5/1999 | Webb | |
| 5,928,389 A | 7/1999 | Jevtic | |
| 5,932,100 A | 8/1999 | Yager et al. | |
| 5,934,856 A | 8/1999 | Asakawa et al. | |
| 5,934,991 A | 8/1999 | Rush | |
| 5,943,721 A | 8/1999 | Lerette et al. | |
| 5,946,945 A | 9/1999 | Kegler et al. | |
| 5,970,554 A | 10/1999 | Shore et al. | |
| 5,971,714 A | 10/1999 | Schaffer et al. | |
| 5,975,492 A | 11/1999 | Brenes | |
| 5,979,306 A | 11/1999 | Fujikawa et al. | |
| 5,980,648 A | 11/1999 | Adler | |
| 5,981,399 A | 11/1999 | Kawamura et al. | |
| 5,989,342 A | 11/1999 | Ikeda et al. | |
| 6,005,226 A | 12/1999 | Aschner et al. | |
| 6,010,315 A | 1/2000 | Kishimoto et al. | 417/228 |
| 6,017,820 A | 1/2000 | Ting et al. | |
| 6,029,371 A | 2/2000 | Kamikawa et al. | |
| 6,035,871 A | 3/2000 | Eui-Yeol | |
| 6,037,277 A | 3/2000 | Masakara et al. | |
| 6,041,817 A | 3/2000 | Guertin | |
| 6,045,331 A | 4/2000 | Gehm et al. | |
| 6,048,494 A | 4/2000 | Annapragada | |
| 6,053,348 A | 4/2000 | Morch | |

| | | |
|---|---|---|
| 6,056,008 A | 5/2000 | Adams et al. |
| 6,062,853 A | 5/2000 | Shimazu et al. |
| 6,067,728 A | 5/2000 | Farmer et al. |
| 6,070,440 A | 6/2000 | Malchow et al. |
| 6,077,053 A | 6/2000 | Fujikawa et al. |
| 6,077,321 A | 6/2000 | Adachi et al. |
| 6,082,150 A | 7/2000 | Stucker |
| 6,085,935 A | 7/2000 | Malchow et al. |
| 6,089,377 A | 7/2000 | Shimizu |
| 6,095,741 A | 8/2000 | Kroeker et al. ............... 414/217 |
| 6,097,015 A | 8/2000 | McCullough et al. |
| 6,103,638 A | 8/2000 | Robinson ..................... 438/778 |
| 6,122,566 A | 9/2000 | Nguyen et al. |
| 6,123,510 A | 9/2000 | Greer et al. |
| 6,128,830 A | 10/2000 | Bettcher et al. |
| 6,145,519 A | 11/2000 | Konishi et al. |
| 6,159,295 A | 12/2000 | Maskara et al. |
| 6,164,297 A | 12/2000 | Kamikawa |
| 6,186,722 B1 | 2/2001 | Shirai |
| 6,190,459 B1 | 2/2001 | Takeshita et al. ............. 118/715 |
| 6,203,582 B1 | 3/2001 | Berner et al. |
| 6,216,364 B1 | 4/2001 | Tanaka et al. |
| 6,221,781 B1 | 4/2001 | Siefering et al. |
| 6,228,563 B1 | 5/2001 | Starov et al. |
| 6,235,634 B1 | 5/2001 | White et al. |
| 6,239,038 B1 | 5/2001 | Wen |
| 6,241,825 B1 | 6/2001 | Wytman |
| 6,244,121 B1 | 6/2001 | Hunter |
| 6,251,250 B1 | 6/2001 | Keigler |
| 6,264,003 B1 | 7/2001 | Dong et al. ............... 184/104.1 |
| 6,264,752 B1 | 7/2001 | Curtis et al. |
| 6,264,753 B1 | 7/2001 | Chao et al. |
| 6,277,753 B1 | 8/2001 | Mullee et al. |
| 6,286,231 B1 | 9/2001 | Bergman et al. |
| 6,305,677 B1 | 10/2001 | Lenz |
| 6,306,564 B1 | 10/2001 | Mullee |
| 6,333,268 B1 | 12/2001 | Starov et al. |
| 6,334,266 B1 | 1/2002 | Moritz |
| 6,344,174 B1 | 2/2002 | Miller et al. |
| 6,347,918 B1 | 2/2002 | Blahnik ..................... 414/217 |
| 6,355,072 B1 | 3/2002 | Racette et al. |
| 6,358,673 B1 | 3/2002 | Namatsu ..................... 430/311 |
| 6,363,292 B1 | 3/2002 | McLoughlin |
| 6,388,317 B1 | 5/2002 | Reese |
| 6,389,677 B1 | 5/2002 | Lenz |
| 6,406,782 B2 | 6/2002 | Johnson et al. |
| 6,418,956 B1 | 7/2002 | Bloom |
| 6,431,185 B1 | 8/2002 | Tomita et al. ................ 134/1.3 |
| 6,436,824 B1 | 8/2002 | Chooi et al. |
| 6,446,875 B1 | 9/2002 | Brooks et al. |
| 6,454,519 B1 | 9/2002 | Toshima et al. |
| 6,454,945 B1 | 9/2002 | Weigl et al. |
| 6,464,790 B1 | 10/2002 | Shertinsky et al. |
| 6,497,239 B2 | 12/2002 | Farmer et al. |
| 6,500,605 B1 | 12/2002 | Mullee et al. ................ 430/329 |
| 6,508,259 B1 | 1/2003 | Tseronis et al. ............. 134/105 |
| 6,509,141 B2 | 1/2003 | Mullee ..................... 430/329 |
| 6,521,466 B1 | 2/2003 | Castrucci |
| 6,532,772 B1 | 3/2003 | Robinson ................... 65/182.2 |
| 6,536,450 B1 | 3/2003 | Dolechek ................... 134/108 |
| 6,541,278 B2 | 4/2003 | Morita et al. |
| 6,546,946 B2 | 4/2003 | Dunmire |
| 6,550,484 B1 | 4/2003 | Gopinath et al. |
| 6,558,475 B1 | 5/2003 | Jur et al. |
| 6,561,213 B2 | 5/2003 | Wang et al. |
| 6,561,220 B2 | 5/2003 | McCullough et al. |
| 6,561,481 B1 | 5/2003 | Filonczuk |
| 6,561,767 B2 | 5/2003 | Biberger et al. |
| 6,564,826 B2 | 5/2003 | Shen |
| 6,596,093 B2 | 7/2003 | DeYoung et al. |
| 6,612,317 B2 | 9/2003 | Costantini et al. |
| 6,613,105 B1 | 9/2003 | Moore ..................... 29/25.01 |
| 6,616,414 B2 | 9/2003 | Yoo et al. |
| 6,641,678 B2 | 11/2003 | DeYoung et al. |
| 6,642,140 B1 | 11/2003 | Moore ..................... 438/631 |
| 6,722,642 B1 | 4/2004 | Sutton et al. |
| 6,736,149 B2 | 5/2004 | Biberger et al. |
| 6,764,212 B1 | 7/2004 | Nitta et al. ................. 366/114 |
| 6,764,552 B1 | 7/2004 | Joyce et al. |
| 6,766,810 B1 | 7/2004 | Van Cleemput ............. 134/1.3 |
| 6,805,801 B1 | 10/2004 | Humayun et al. |
| 6,815,922 B2 | 11/2004 | Yoo et al. |
| 6,817,368 B2 | 11/2004 | Toshima et al. ............. 134/95.3 |
| 6,848,458 B1 | 2/2005 | Shrinivasan et al. |
| 6,851,148 B2 | 2/2005 | Preston et al. |
| 6,874,513 B2 | 4/2005 | Yamagata et al. |
| 6,921,456 B2 | 7/2005 | Biberger et al. |
| 6,966,967 B2 | 11/2005 | Curry et al. |
| 2001/0050096 A1 | 12/2001 | Costantini et al. |
| 2002/0001929 A1 | 1/2002 | Biberger |
| 2002/0014257 A1 | 2/2002 | Chandra et al. ................ 134/19 |
| 2002/0046707 A1 | 4/2002 | Biberger et al. |
| 2002/0130137 A1 | 9/2002 | Greenwald et al. |
| 2002/0144713 A1 | 10/2002 | Kuo et al. ..................... 134/18 |
| 2002/0189543 A1 | 12/2002 | Biberger et al. |
| 2003/0005948 A1 | 1/2003 | Matsuno et al. |
| 2003/0029479 A1 | 2/2003 | Asano ......................... 134/18 |
| 2003/0036023 A1 | 2/2003 | Moreau et al. |
| 2003/0051741 A1 | 3/2003 | DeSimone et al. |
| 2003/0081206 A1 | 5/2003 | Doyle ......................... 356/301 |
| 2003/0161734 A1 | 8/2003 | Kim |
| 2003/0196679 A1 | 10/2003 | Cotte et al. |
| 2003/0205510 A1 | 11/2003 | Jackson |
| 2004/0011386 A1 | 1/2004 | Seghal |
| 2004/0020518 A1 | 2/2004 | DeYoung et al. |
| 2004/0045588 A1 | 3/2004 | DeYoung et al. ............... 134/26 |
| 2004/0055624 A1 | 3/2004 | McDermott et al. |
| 2004/0099604 A1 | 5/2004 | Hauck et al. ................. 210/656 |
| 2004/0103922 A1 | 6/2004 | Inoue et al. .................... 134/26 |
| 2004/0118281 A1 | 6/2004 | Leitch et al. |
| 2004/0118812 A1 | 6/2004 | Watkins et al. ................. 216/83 |
| 2004/0134515 A1 | 7/2004 | Castrucci |
| 2004/0157463 A1 | 8/2004 | Jones |
| 2004/0168709 A1* | 9/2004 | Drumm et al. ................. 134/18 |
| 2004/0211440 A1 | 10/2004 | Wang et al. ..................... 134/2 |
| 2004/0213676 A1 | 10/2004 | Phillips et al. |
| 2004/0221875 A1 | 11/2004 | Saga et al. .................... 134/26 |
| 2004/0245489 A1 | 12/2004 | Kurita et al. ................... 251/95 |
| 2004/0255978 A1 | 12/2004 | Fury et al. .................... 134/18 |
| 2005/0014370 A1 | 1/2005 | Jones |
| 2005/0026547 A1 | 2/2005 | Moore et al. |
| 2005/0111987 A1 | 5/2005 | Yoo et al. |
| 2005/0141998 A1 | 6/2005 | Yoo et al. |
| 2005/0158178 A1 | 7/2005 | Yoo et al. |
| 2005/0191184 A1 | 9/2005 | Vinson, Jr. |
| 2006/0102204 A1 | 5/2006 | Jacobson et al. ............... 134/26 |
| 2006/0102208 A1 | 5/2006 | Jacobson et al. ............... 134/56 |
| 2006/0130966 A1 | 6/2006 | Babic et al. |
| 2006/0177362 A1 | 8/2006 | D'Evelyn et al. ........... 422/245.1 |
| 2006/0180175 A1 | 8/2006 | Parent ....................... 134/1.3 |

FOREIGN PATENT DOCUMENTS

| | | |
|---|---|---|
| DE | 36 08 783 A1 | 9/1987 |
| DE | 198 60 084 A1 | 7/2000 |
| EP | 0 244 951 A2 | 11/1987 |
| EP | 0 272 141 A2 | 6/1988 |
| EP | 0408216 A2 | 1/1991 |
| EP | 0 453 867 A1 | 10/1991 |
| EP | 0 572 913 A1 | 12/1993 |
| EP | 0 587 168 A1 | 3/1994 |
| EP | 0 679 753 B1 | 11/1995 |
| EP | 0 726 099 A2 | 8/1996 |
| EP | 0 743 379 A1 | 11/1996 |
| EP | 0822583 A2 | 4/1998 |
| EP | 0 903 775 A2 | 3/1999 |

| | | |
|---|---|---|
| FR | 1.499.491 | 9/1967 |
| GB | 2 003 975 | 3/1979 |
| GB | 2 193 482 | 2/1988 |
| JP | 56-142629 | 11/1981 |
| JP | 60-238479 | 11/1985 |
| JP | 60-246635 | 12/1985 |
| JP | 61-017151 | 1/1986 |
| JP | 61-231166 | 10/1986 |
| JP | 62-111442 | 5/1987 |
| JP | 62-125619 | 6/1987 |
| JP | 63-179530 | 7/1988 |
| JP | 63-256326 | 10/1988 |
| JP | 63-303059 | 12/1988 |
| JP | 2-122520 | 5/1990 |
| JP | 2-148841 | 6/1990 |
| JP | 2-209729 | 8/1990 |
| JP | 03-080537 | 4/1991 |
| JP | 4-14222 | 1/1992 |
| JP | 4-17333 | 1/1992 |
| JP | 4-284648 | 10/1992 |
| JP | 5-283511 | 10/1993 |
| JP | 7-24679 | 3/1995 |
| JP | 7-283104 | 10/1995 |
| JP | 8-186140 | 7/1996 |
| JP | 8-252549 | 10/1996 |
| JP | 8-306632 | 11/1996 |
| JP | 9-43857 | 2/1997 |
| JP | 10-135170 | 5/1998 |
| JP | 10-144757 | 5/1998 |
| JP | 10-260537 | 9/1998 |
| JP | 10-335408 | 12/1998 |
| JP | 11-200035 | 7/1999 |
| JP | 11-204514 | 7/1999 |
| JP | 11-260809 | 9/1999 |
| JP | 11-274132 | 10/1999 |
| JP | 2000/106358 | 4/2000 |
| JP | 2001/77074 | 3/2001 |
| SE | 251213 | 8/1948 |
| TW | 492060 | 6/2002 |
| TW | 492100 | 6/2002 |
| TW | 499696 | 8/2002 |
| WO | WO 87/07309 | 12/1987 |
| WO | WO 91/12629 | 8/1991 |
| WO | WO 99/18603 | 4/1999 |
| WO | WO 00/36635 | 6/2000 |
| WO | WO 01/10733 A1 | 2/2001 |
| WO | WO 01/22016 A1 | 3/2001 |
| WO | WO 01/33615 A3 | 5/2001 |
| WO | WO 01/55628 A1 | 8/2001 |
| WO | WO 01/68279 A2 | 9/2001 |
| WO | WO 01/74538 A1 | 10/2001 |
| WO | WO 01/78911 A1 | 10/2001 |
| WO | WO 01/85391 A2 | 11/2001 |
| WO | WO 01/94782 A3 | 12/2001 |
| WO | WO 02/09147 A2 | 1/2002 |
| WO | WO 02/16051 A2 | 2/2002 |
| WO | WO 02/084709 A2 | 10/2002 |
| WO | WO 03/030219 A2 | 10/2003 |

OTHER PUBLICATIONS

Sun, Y.P. et al., "Preparation of Polymer-Protected Semiconductor Nanoparticles Through the Rapid Expansion of Supercritical Fluid Solution," Chemical Physics Letters, pp. 585-588, May 22, 1998.

Dahmen, N. et al., "Supercritical Fluid Extraction of Grinding and Metal Cutting Waste Contaminated with Oils," Supercritical Fluids—Extraction and Pollution Prevention, ACS Symposium Series, vol. 670, pp. 270-279, Oct. 21, 1997.

Xu, C. et al., "Submicron-Sized Spherical Yttrium Oxide Based Phosphors Prepared by Supercritical CO2-Assisted aerosolization and pyrolysis," Appl. Phys. Lett., vol. 71, No. 12, Sep. 22, 1997, pp. 1643-1645.

Courtecuisse, V.G. et al., "Kinetics of the Titanium Isopropoxide Decomposition in Supercritical Isopropyl Alcohol," Ind. Eng. Chem. Res., vol. 35, No. 8, pp. 2539-2545, Aug. 1996.

Gallagher-Wetmore, P. et al., "Supercritical Fluid Processing: A New Dry Technique for Photoresist Developing," SPIE vol. 2438, pp. 694-708, Jun. 1995.

McHardy, J. et al., "Progress in Supercritical CO2 Cleaning," SAMPE Jour., vol. 29, No. 5, pp. 20-27, Sep. 1993.

Purtell, R, et al., "Precision Parts Cleaning Using Supercritical Fluids," J. Vac, Sci, Technol. A. vol. 11, No. 4, Jul. 1993, pp. 1696-1701.

Hansen, B.N. et al., "Supercritical Fluid Transport—Chemical Deposition of Films,"Chem. Mater., vol. 4, No. 4, pp. 749-752, 1992.

Hybertson, B.M. et al., "Deposition of Palladium Films by a Novel Supercritical Fluid Transport Chemical Deposition Process," Mat. Res. Bull., vol. 26, pp. 1127-1133, 1991.

Ziger, D. H. et al., "Compressed Fluid Technology: Application to RIE-Developed Resists," AiChE Jour., vol. 33, No. 10, pp. 1585-1591, Oct. 1987.

Matson, D.W. et al., "Rapid Expansion of Supercritical Fluid Solutions: Solute Formation of Powders, Thin Films, and Fibers," Ind. Eng. Chem. Res., vol. 26, No. 11, pp. 2298-2306, 1987.

Tolley, W.K. et al., "Stripping Organics from Metal and Mineral Surfaces using Supercritical Fluids," Separation Science and Technology, vol. 22, pp. 1087-1101, 1987.

Joseph L. Foszcz, "Diaphragm Pumps Eliminate Seal Problems", Plant Engineering, pp. 1-5, Feb. 1, 1996.

Bob Agnew, "Wilden Air-Operated Diaphragm Pumps", Process & Industrial Training Technologies, Inc., 1996.

* cited by examiner

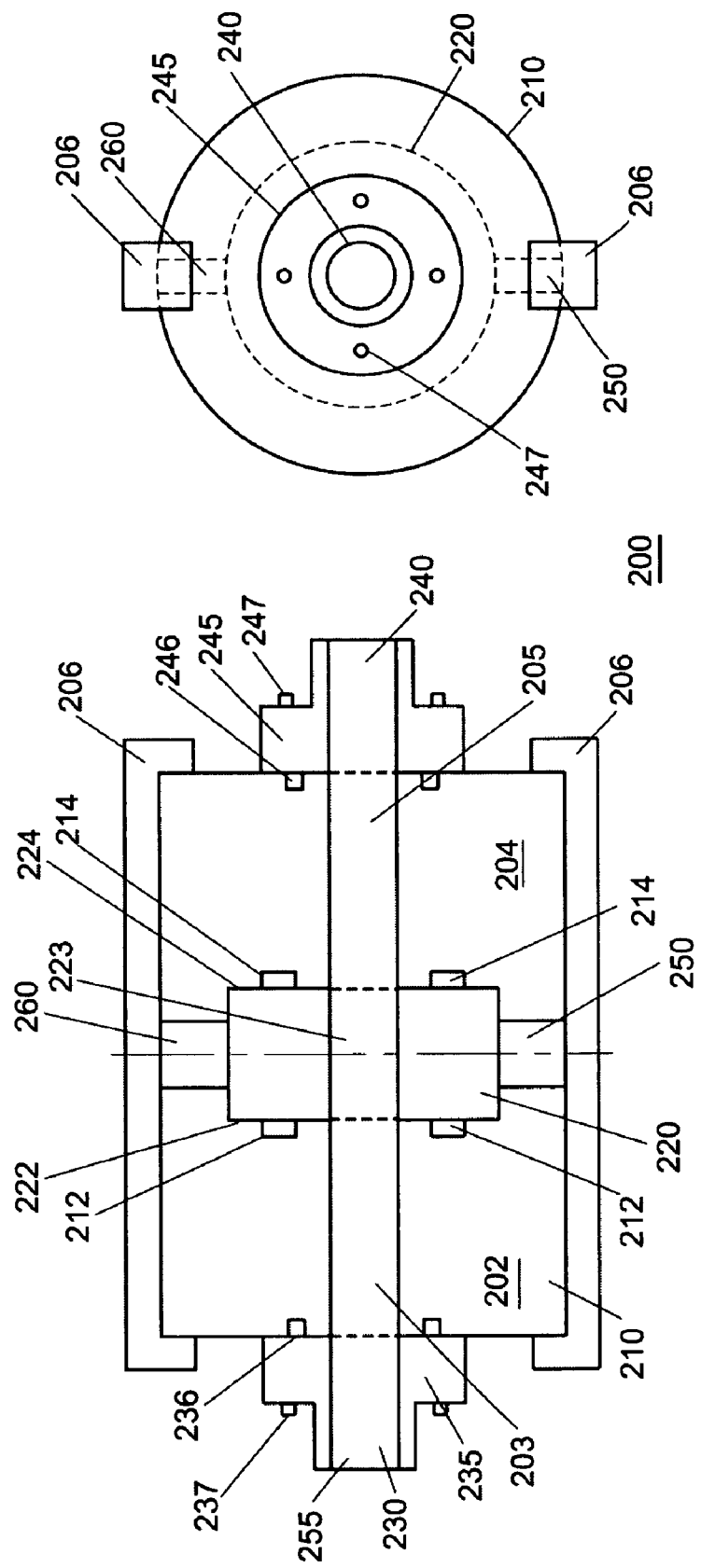

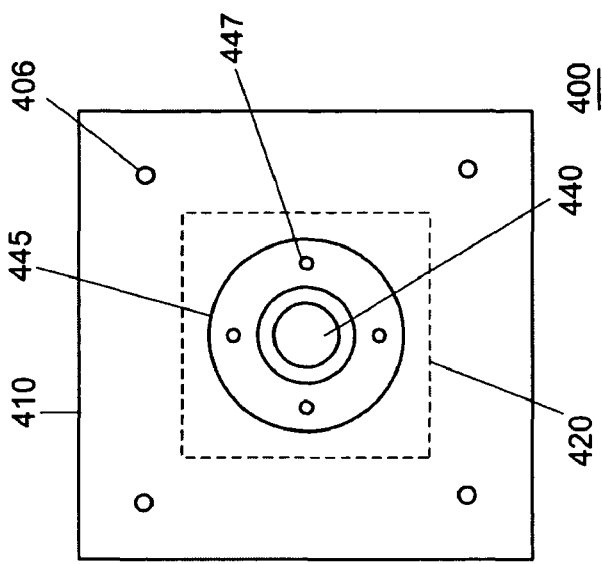
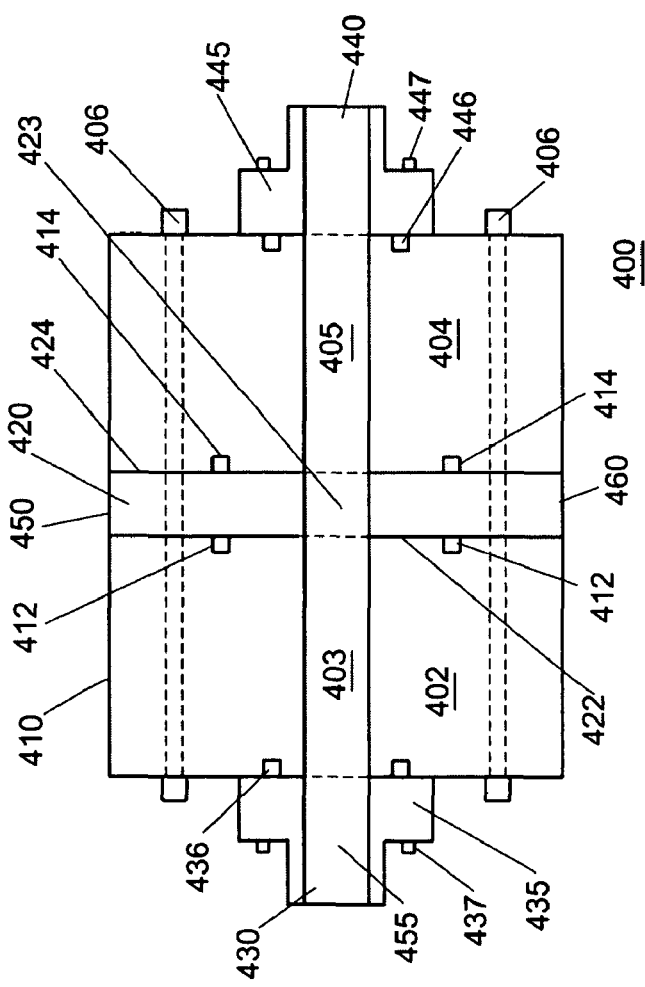
FIG. 4B
FIG. 4A

US 7,767,145 B2

HIGH PRESSURE FOURIER TRANSFORM INFRARED CELL

CROSS-REFERENCE TO RELATED APPLICATIONS

This patent application is related to commonly owned co-pending U.S. patent application Ser. No. 11/065,636, filed Feb. 23, 2005, entitled "IMPROVED RINSING STEP IN SUPERCRITICAL PROCESSING", U.S. patent application Ser. No. 11/065,377, filed Feb. 23, 2005, entitled "IMPROVED CLEANING STEP IN SUPERCRITICAL PROCESSING", U.S. patent application Ser. No. 11/065,376, filed Feb. 23, 2005, entitled "ETCHING AND CLEANING BPSG MATERIAL USING SUPERCRITICAL PROCESSING", and U.S. patent application Ser. No. 11/0,923,232, filed Mar. 25, 2005, entitled "PROCESS FLOW THERMOCOUPLE", which are hereby incorporated by reference in its entirety.

FIELD OF THE INVENTION

The present invention relates to the field of micro-device manufacturing equipment and processing. More particularly, the present invention relates to the field of monitoring a solution in situ within a high pressure environment.

BACKGROUND OF THE INVENTION

Semiconductor wafer processing typically can be carried out at non-standard temperature and pressure, such as vacuum, sub atmospheric pressure, or over pressure environments. Solutions used in processing wafers such as etchants and reactants, are composed of varied chemistries, both simple and complex. Often, obtaining an exact chemistry composition is critical to the success of a process step. Unfortunately, the nature of the processing environment is that the process steps are performed within sealed environments, to control the processing environment and obtain the desired chemistry. Such a sealed environment is not conducive for monitoring and analyzing conditions within the sealed environment, in particular the solution contained within the sealed environment. There exists a need to better monitor and analyze a solution within a sealed environment. Monitoring and analyzing high pressured sealed environments are particularly difficult, and dangerous, due to the nature of the high pressure. There is therefore also a need to better monitor and analyze a solution within a high pressure sealed environment.

In semiconductor manufacturing, defects and other problems are observed on output wafers. Such wafer defects are often attributable to improper solution process chemistries and environments used in the wafer process steps. Although process engineers are aware of external elements added to the processing environment, it is often unknown what residual chemistries exist in the processing environment prior to the introduction of the external elements. Attempts to completely clean a processing environment seldom if ever result in a 100% clean environment. Therefore, despite efforts to clean the processing environment, an unknown amount of residual elements remain prior to each new processing step. There exists a need to monitor the conditions within a closed environment to account for both residual and externally added elements.

A conventional monitoring practice for closed loop environments includes collecting exhaust generated from the processing environment. Unfortunately, collecting exhaust does not provide real time measurements of the processing environment. There is a need to monitor and analysis a closed loop processing environment in real time.

SUMMARY OF THE INVENTION

In an aspect of the present invention, a system monitors a solution within a high pressure environment. The system comprises a closed loop to transport the solution, the closed loop including the high pressure environment, a material block substantially transparent to a light output, wherein the material block is positioned at a point in the closed loop, a light source to emit the light output, the light output directed to a first side of the material block, and a light detector to receive the light output out of a second side of the material block such that the light output passes through the first side of the material block, through the solution, and through the second side of the material block to the light detector. The system can further comprise an analyzing device coupled to the light detector to receive the light output received by the light detector and to analyze a composition of the solution based on the light output received. The solution can be under high pressure. The light source and the light detector are outside the high pressure environment. The light source can be an infrared light source. The light detector can be an infrared light detector. The material block can be substantially transparent to infrared. The material block can comprise calcium fluoride. The material block can comprise a diameter defined by the first side of the material block and the second side of the material block, and a thickness defined by a first surface of the material block and a second surface of the material block, the diameter greater than the thickness. The material block can further comprise a hole through the thickness from the first surface to the second surface, wherein the hole is approximately centered along the diameter. The light output can be transmitted through the diameter of the material block.

The closed loop can include a first fluid line having a first end and a second fluid line having a second end, the first end coupled to the first surface of the material block and the second end coupled to the second surface of the material block at the hole. The system can further comprise a first collar for coupling the first end of the first fluid line to the first surface of the material block, and a second collar for coupling the second end of the second fluid line to the second surface of the material block. The system can further comprise at least one clamp for securing the first collar to the second collar. The system can further comprise a first o-ring seal to seal the first collar to the first surface of the material block, and a second o-ring seal to seal the second collar to the second surface of the material block. The system can also comprise at least one clamp for securing the first collar to the first fluid line, and at least one clamp for securing the second collar to the second fluid line. A hole diameter can be approximately the same as a first fluid line diameter and a second fluid line diameter.

The received light output can be analyzed using Fourier Transform. The material block can comprise a disk of calcium fluoride including a hole through a thickness of the disk through which the solution passes. The material block can include two pieces of material substantially transparent to the light output, one piece positioned between the light source and the solution and a second piece positioned between the solution and the light detector. The system can further comprise a securing mechanism to secure the two pieces of substantially transparent material in place without blocking a path of the light beam from the light source to the light detector through the two pieces of substantially transparent material.

In another aspect of the present invention, a transparent cell enables analysis of a solution in a high pressure environment. The transparent cell comprises a block of material substantially transparent to a light beam, wherein the block material includes a hole through which the solution passes. A first collar is coupled to a first surface of the block material to couple a first fluid line to the first surface at the hole. A second collar is coupled to a second surface of the block material to couple a second fluid line to the second surface at the hole. This enables the solution to pass from the first fluid line through the hole of the block material to the second fluid line. The light beam is also enabled to enter the transparent cell at a first side of the material block, pass through the solution at the hole of the material block and exit the transparent cell at a second side of the material block. The means for clamping the first collar to the second collar secures the block of material in place.

The light beam can be infrared. The material block can be substantially transparent to infrared light. The material block can comprise calcium fluoride.

The material block can comprise a diameter defined by the first side of the material block and the second side of the material block, and a thickness defined by the first surface of the material block and the second surface of the material block, where the diameter is greater than the thickness. The hole can pass through the thickness from the first surface to the second surface. The hole is approximately centered along the diameter. The light beam can be transmitted through the diameter of the material block. The transparent cell can further comprise a first o-ring seal to seal the first collar to the first surface of the material block, and a second o-ring seal to seal the second collar to the second surface of the material block. The transparent cell can further comprise means for clamping the first collar to the first fluid line, and means for clamping the second collar to the second fluid line. A hole diameter can be approximately the same as a first fluid line diameter and a second fluid line diameter. The material block can comprise a disk of calcium fluoride including the hole through approximately a center thickness of the disk. The material block can include two pieces of material substantially transparent to the light beam, a first piece positioned between a light source of the light and the solution and a second piece positioned on an opposite side of the solution from the first piece. The transparent cell can further comprise a securing mechanism to secure the two pieces of substantially transparent material in place without blocking a path of the light beam through the transparent cell via the two pieces of substantially transparent material.

In yet another aspect of the present invention, a method analyzes a high-pressure solution within a closed loop environment. The method comprises circulating the high pressure solution through a closed loop, the closed loop including a transparent cell through which the solution passes, the transparent cell including a block material that is substantially transparent to a light beam, directing the light beam at a first side of the block material such that the light beam passes through the block material and the solution passing therethrough, receiving the light beam output from a second side of the block material, and analyzing the received light beam. The method can further comprise altering a composition of the solution based on the analysis of the received light beam. The received light beam can comprise infrared light and analyzing the infrared light is performed using Fourier Transform. The method can further comprise configuring the closed loop to include the transparent cell by securing a transparent disk of block material to a first fluid line and to a second fluid line. The method can further comprise configuring the transparent disk to include a hole through which the solution passes.

BRIEF DESCRIPTION OF THE DRAWINGS

A more complete appreciation of various embodiments of the invention and many of the attendant advantages thereof will become readily apparent with reference to the following detailed description, particularly when considered in conjunction with the accompanying drawings, in which:

FIGS. 2A and 2B illustrate a simplified cross sectional view of a monitoring system in accordance with an embodiment of the invention;

FIGS. 4A and 4B illustrate a simplified cross sectional view of another monitoring system in accordance with the invention;

DETAILED DESCRIPTION OF SEVERAL EMBODIMENTS

Figure 1:
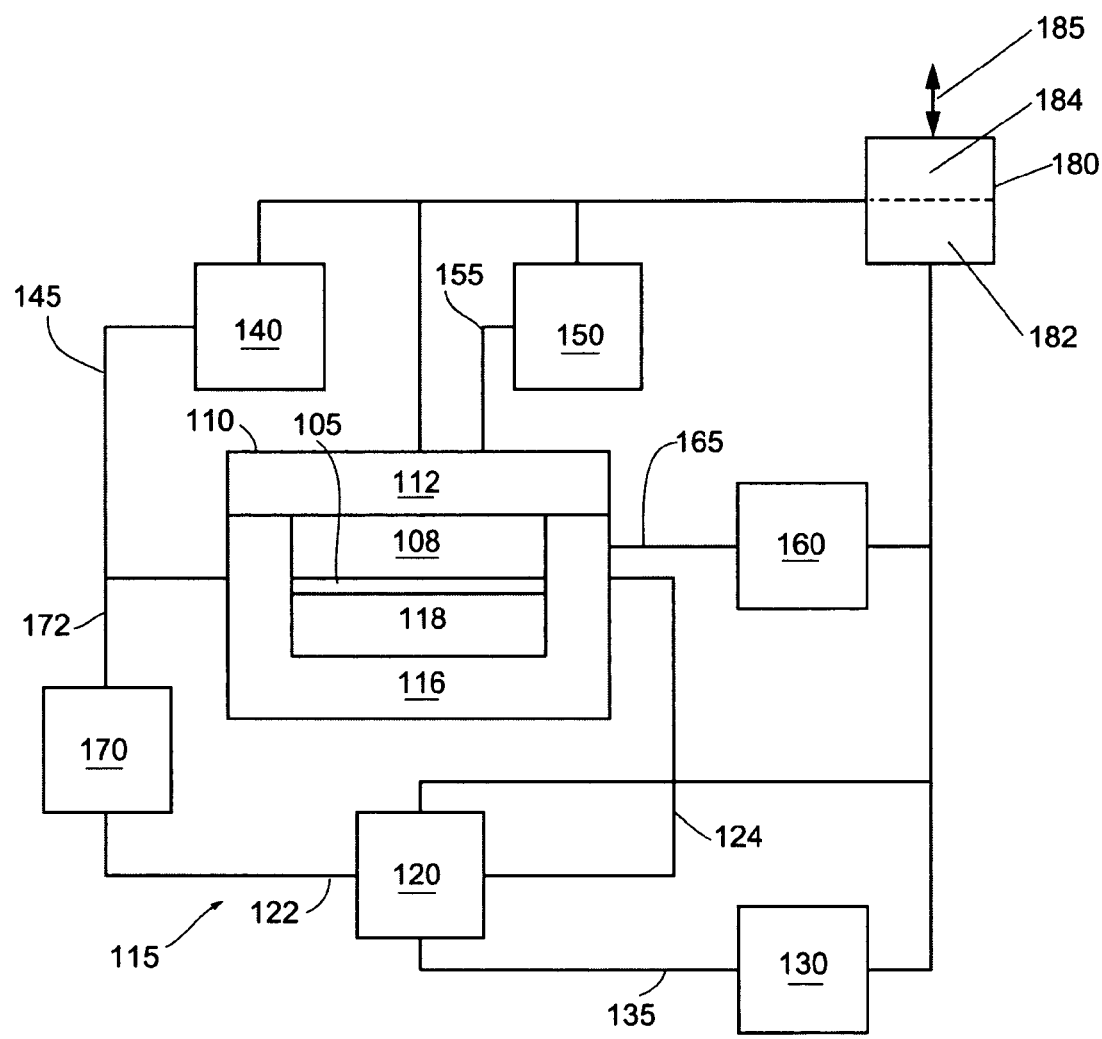
FIG. 1 shows an exemplary block diagram of a processing system in accordance with embodiments of the invention.

Embodiments of the present invention disclose a transparent cell that enables in situ monitoring of a solution enclosed within a closed loop environment. The transparent cell is preferably applied to the semiconductor industry which require specific solution compositions during one or more processing steps. The closed loop environment is preferably under high pressure. In the preferred embodiment, the high pressure system can exceed 3,000 psi.

The transparent cell includes a block of material that is substantially transparent to an external light source. The material block preferably comprises a calcium fluoride disk that is substantially transparent to infrared light. The calcium fluoride disk is preferably configured such that the diameter is longer than the thickness. The thickness is measured by the distance from a top surface of the disk to a bottom surface on the opposite side of the disk. A hole is preferably configured through the thickness of the disk, at the diameter center. The closed loop environment includes a fluid line through which the solution is transported under pressure. The calcium fluoride disk is inserted within the fluid line such that a first end of the fluid line is attached to the disk at one end of the hole and a second end of the fluid line is attached to the disk at the other end of the hole. In this manner, the solution within the fluid line is directed out of the first end of the fluid line, through the hole in the calcium fluoride disk, and in through the second end of the fluid line. The first end of the fluid line is preferably clamped to the top surface of the disk, and the second end of the fluid line is preferably clamped to second surface of the disk using conventional clamping means.

Solution passing through the hole of the calcium fluoride disk is analyzed by directing infrared light through the disk along its diameter. In this manner, a light beam enters the disk at a first point along its perimeter, passes through the disk along its diameter while also passing through the solution currently moving through the hole in the disk, and exits the disk at a second point along its perimeter. The first point and the second point are on opposite ends of the disk's diameter. The light exiting the disk is collected, preferably by a light detector. The collected light is then analyzed to determine the composition of the solution through which the light passed.

The transparent cell is preferably used in a system for treating a substrate material with a supercritical cleaning solution. Further details of supercritical systems suitable for cleaning post-etch residues from wafer substrates are described in U.S. patent application Ser. No. 09/389,788, filed Sep. 3, 1999, and entitled "REMOVAL OF PHOTORESIST AND PHOTORESIST RESIDUE FROM SEMICONDUCTORS USING SUPERCRITICAL CARBON DIOXIDE PROCESS" and U.S. patent application Ser. No. 09/697,222, filed Oct. 25, 2000, and entitled "REMOVAL OF PHOTORESIST AND RESIDUE FROM SUBSTRATE USING SUPERCRITICAL CARBON DIOXIDE PROCESS", both of which are hereby incorporated by reference. Alternatively, the transparent cell can be used in any closed loop environment in which a solution internal to the closed loop environment is to be monitored.

FIG. 1 shows an exemplary block diagram of a processing system in accordance with an embodiment of the invention. In the illustrated embodiment, processing system 100 comprises a process module 110, a recirculation system 120, a process chemistry supply system 130, a high-pressure fluid supply system 140, an exhaust control system 150, a pressure control system 160, a monitoring system 170, and a controller 180. The processing system 100 can operate at pressures that can range from 1000 psi. to 10,000 psi. In addition, the processing system 100 can operate at temperatures that can range from 40 to 300 degrees Celsius.

The details concerning one example of a processing chamber are disclosed in co-owned and co-pending U.S. patent applications, Ser. No. 09/912,844, entitled "HIGH PRESSURE PROCESSING CHAMBER FOR SEMICONDUCTOR SUBSTRATE," filed Jul. 24, 2001, Ser. No. 09/970,309, entitled "HIGH PRESSURE PROCESSING CHAMBER FOR MULTIPLE SEMICONDUCTOR SUBSTRATES," filed Oct. 3, 2001, Ser. No. 10/121,791, entitled "HIGH PRESSURE PROCESSING CHAMBER FOR SEMICONDUCTOR SUBSTRATE INCLUDING FLOW ENHANCING FEATURES," filed Apr. 10, 2002, and Ser. No. 10/364,284, entitled "HIGH-PRESSURE PROCESSING CHAMBER FOR A SEMICONDUCTOR WAFER," filed Feb. 10, 2003, the contents of which are incorporated herein by reference.

The controller 180 can be coupled to the process module 110, the recirculation system 120, the process chemistry supply system 130, the high-pressure fluid supply system 140, the exhaust control system 150, the pressure control system 160, and the monitoring system 170. Alternately, controller 180 can be coupled to one or more additional controllers/computers (not shown), and controller 180 can obtain setup, configuration, and/or recipe information from an additional controller/computer.

In FIG. 1, singular processing elements (110,120, 130, 140,150, 160, 170, and 180) are shown, but this is not required for the invention. The semiconductor processing system 100 can comprise any number of processing elements having any number of controllers associated with them in addition to independent processing elements.

The controller 180 can be used to configure any number of processing elements (110, 120, 130, 140, 150,160, and 170), and the controller 180 can collect, provide, process, store, and display data from processing elements. The controller 180 can comprise a number of applications for controlling one or more of the processing elements. For example, controller 180 can include a GUI component (not shown) that can provide easy to use interfaces that enable a user to monitor and/or control one or more processing elements.

The process module 110 can include an upper assembly 112 and a lower assembly 116, and the upper assembly 112 can be coupled to the lower assembly 116. In an alternate embodiment, a frame and or injection ring may be included and may be coupled to an upper assembly and a lower assembly. The upper assembly 112 can comprise a heater (not shown) for heating the process chamber, the substrate, or the processing fluid, or a combination of two or more thereof. Alternately, a heater is not required in the upper assembly 112. In another embodiment, the lower assembly 116 can comprise a heater (not shown) for heating the process chamber, the substrate, or the processing fluid, or a combination of two or more thereof. The process module 110 can include means for flowing a processing fluid through the processing chamber 108. In one example, a circular flow pattern can be established, and in another example, a substantially linear flow pattern can be established. Alternately, the means for flowing can be configured differently. The lower assembly 116 can comprise one or more lifters (not shown) for moving the chuck 118 and/or the substrate 105. Alternately, a lifter is not required.

In one embodiment, the process module 110 can include a holder or chuck 118 for supporting and holding the substrate 105 while processing the substrate 105. The holder or chuck 118 can also be configured to heat or cool the substrate 105 before, during, and/or after processing the substrate 105. Alternately, the process module 110 can include a platen for supporting and holding the substrate 105 while processing the substrate 105.

A transfer system (not shown) can be used to move a substrate into and out of the processing chamber 108 through a slot (not shown). In one example, the slot can be opened and closed by moving the chuck, and in another example, the slot can be controlled using a gate valve.

The substrate can include semiconductor material, metallic material, dielectric material, ceramic material, or polymer material, or a combination of two or more thereof. The semiconductor material can include Si, Ge, Si/Ge, or GaAs. The metallic material can include Cu, Al, Ni, Pb, Ti, Ta, or W, or combinations of two or more thereof. The dielectric material can include Si, O, N, H, P, or C, or combinations of two or more thereof. The ceramic material can include Al, N, Si, C, or O, or combinations of two or more thereof.

In one embodiment, the processing system 100 can comprise a monitoring system 170. As shown in the illustrated embodiment, the monitoring system 170 is coupled to the process module 110 using one or more flow lines 172 and is coupled to the recirculation system 120 using one or more inlet lines 122. In addition, the recirculation system 120 can be coupled to the process module 110 using one or more outlet lines 124. A recirculation loop 115 can be configured that includes a portion of the recirculation system 120, a portion of the process module 110, a portion of the monitoring system, one or more of the flow lines 172, one or more of the inlet lines 122, and one or more of the outlet lines 124. In one embodiment, the recirculation loop 115 comprises a volume of approximately one liter. In alternate embodiments, the volume of the recirculation loop 115 can vary from approximately 0.5 liters to approximately 2.5 liters. The monitoring system 170 can comprise means (not shown) for monitoring the chemical composition of the fluid flowing in the recirculation loop 115.

The recirculation system 120 can comprise one or more pumps (not shown), can be used to regulate the flow of the supercritical processing solution through the processing chamber 108 and the other elements in the recirculation loop 115. The flow rate can vary from approximately 0.01 liters/minute to approximately 100 liters/minute.

The recirculation system 120 can comprise one or more valves (not shown) for regulating the flow of a supercritical processing solution through the recirculation loop 115. For example, the recirculation system 120 can comprise any number of back-flow valves, filters, pumps, and/or heaters (not shown) for maintaining a supercritical processing solution and flowing the supercritical process solution through the recirculation system 120 and through the processing chamber 108 in the process module 110.

Processing system 100 can comprise a process chemistry supply system 130. In the illustrated embodiment, the process chemistry supply system 130 is coupled to the recirculation system 120 using one or more lines 135, but this is not required for the invention. In alternate embodiments, the process chemistry supply system can be configured differently and can be coupled to different elements in the processing system.

The process chemistry is introduced by the process chemistry supply system 130 into the fluid introduced by the high-pressure fluid supply system 140 at ratios that vary with the substrate properties, the chemistry being used, and the process being performed in the processing chamber 110. The ratio can vary from approximately 0.001 to approximately 15 percent by volume. For example, when the recirculation loop 115 comprises a volume of about one liter, the process chemistry volumes can range from approximately ten microliters to approximately one hundred fifty milliliters. In alternate embodiments, the volume and/or the ratio may be higher or lower.

The process chemistry supply system 130 can comprise a cleaning chemistry assembly (not shown) for providing cleaning chemistry for generating supercritical cleaning solutions within the processing chamber. The cleaning chemistry can include peroxides and a fluoride source. For example, the peroxides can include hydrogen peroxide, benzoyl peroxide, or any other suitable peroxide, and the fluoride sources can include fluoride salts (such as ammonium fluoride salts), hydrogen fluoride, fluoride adducts (such as organic-ammonium fluoride adducts) and combinations thereof.

Further details of fluoride sources and methods of generating supercritical processing solutions with fluoride sources are described in U.S. patent application Ser. No. 10/442,557, filed May 10, 2003, and titled "TETRA-ORGANIC AMMONIUM FLUORIDE AND HF IN SUPERCRITICAL FLUID FOR PHOTORESIST AND RESIDUE REMOVAL", and U.S. patent application Ser. No. 10/321,341, filed Dec. 16, 2002, and titled "FLUORIDE IN SUPERCRITICAL FLUID FOR PHOTORESIST POLYMER AND RESIDUE REMOVAL," both are incorporated by reference herein.

In addition, the cleaning chemistry can include chelating agents, complexing agents, oxidants, organic acids, and inorganic acids that can be introduced into supercritical carbon dioxide with one or more carrier solvents, such as N,N-dimethylacetamide (DMAc), gamma-butyrolactone (BLO), dimethyl sulfoxide (DMSO), ethylene carbonate (EC), N-methylpyrrolidone (NMP), dimethylpiperidone, propylene carbonate, and alcohols (such a methanol, ethanol and 1-propanol).

Furthermore, the cleaning chemistry can include solvents, co-solvents, surfactants, and/or other ingredients. Examples of solvents, co-solvents, and surfactants are disclosed in co-owned U.S. Pat. No. 6,500,605, entitled "REMOVAL OF PHOTORESIST AND RESIDUE FROM SUBSTRATE USING SUPERCRITICAL CARBON DIOXIDE PROCESS", issued Dec. 31, 2002, and U.S. Pat. No. 6,277,753, entitled "REMOVAL OF CMP RESIDUE FROM SEMICONDUCTORS USING SUPERCRITICAL CARBON DIOXIDE PROCESS", issued Aug. 21, 2001, both are incorporated by reference herein.

The process chemistry supply system 130 can be configured to introduce N-methyl pyrrolidone (NMP), diglycol amine, hydroxyl amine, di-isopropyl amine, tri-isoprpyl amine, tertiary amines, catechol, ammonium fluoride, ammonium bifluoride, methylacetoacetamide, ozone, propylene glycol monoethyl ether acetate, acetylacetone, dibasic esters, ethyl lactate, $CHF_3$, $BF_3$, HF, other fluorine containing chemicals, or any mixture thereof. Other chemicals such as organic solvents may be utilized independently or in conjunction with the above chemicals to remove organic materials. The organic solvents may include, for example, an alcohol, ether, and/or glycol, such as acetone, diacetone alcohol, dimethyl sulfoxide (DMSO), ethylene glycol, methanol, ethanol, propanol, or isopropanol (IPA). For further details, see U.S. Pat. No. 6,306,564B1, filed May 27, 1998, and titled "REMOVAL OF RESIST OR RESIDUE FROM SEMICONDUCTORS USING SUPERCRITICAL CARBON DIOXIDE", and U.S. Pat. No. 6,509,141B2, filed Sep. 3, 1999, and titled "REMOVAL OF PHOTORESIST AND PHOTORESIST RESIDUE FROM SEMICONDUCTORS USING SUPERCRITICAL CARBON DIOXIDE PROCESS", both are incorporated by reference herein.

Moreover, the process chemistry supply system 130 can be configured to introduce a peroxide during a cleaning and/or rinsing process. The peroxide can be introduced with any one of the above process chemistries, or any mixture thereof. The peroxide can include organic peroxides, or inorganic peroxides, or a combination thereof. For example, organic peroxides can include 2-butanone peroxide; 2,4-pentanedione peroxide; peracetic acid; t-butyl hydroperoxide; benzoyl peroxide; or m-chloroperbenzoic acid (mCPBA). Other peroxides can include hydrogen peroxide. Alternatively, the peroxide can include a diacyl peroxide, such as: decanoyl peroxide; lauroyl peroxide; succinic acid peroxide; or benzoyl peroxide; or any combination thereof. Alternatively, the peroxide can include a dialkyl peroxide, such as: dicumyl peroxide; 2,5-di(t-butylperoxy)-2,5-dimethylhexane; t-butyl cumyl peroxide; α,α-bis(t-butylperoxy)diisopropylbenzene mixture of isomers; di(t-amyl) peroxide; di(t-butyl) peroxide; or 2,5-di(t-butylperoxy)-2,5-dimethyl-3-hexyne; or any combination thereof. Alternatively, the peroxide can include a diperoxyketal, such as: 1,1-di(t-butylperoxy)-3,3,5-trimethylcyclohexane; 1,1-di(t-butylperoxy)cyclohexane; 1,1-di(t-amylperoxy)-cyclohexane; n-butyl 4,4-di(t-butylperoxy)valerate; ethyl 3,3-di-(t-amylperoxy)butanoate; t-butyl peroxy-2-ethylhexanoate; or ethyl 3,3-di(t-butylperoxy)butyrate; or any combination thereof. Alternatively, the peroxide can include a hydroperoxide, such as: cumene hydroperoxide; or t-butyl hydroperoxide; or any combination thereof. Alternatively, the peroxide can include a ketone peroxide, such as: methyl ethyl ketone peroxide; or 2,4-pentanedione peroxide; or any combination thereof. Alternatively, the peroxide can include a peroxydicarbonate, such as: di(n-propyl)peroxydicarbonate; di(sec-butyl)peroxydicarbonate; or di(2-ethylhexyl)peroxydicarbonate; or any combination thereof. Alternatively, the peroxide can include a peroxyester, such as:

3-hydroxyl-1,1-dimethylbutyl peroxyneodecanoate; a-cumyl peroxyneodecanoate; t-amyl peroxyneodecanoate; t-butyl peroxyneodecanoate; t-butyl peroxypivalate; 2,5-di (2-ethylhexanoylperoxy)-2,5-dimethylhexane; t-amyl peroxy-2-ethylhexanoate; t-butyl peroxy-2-ethylhexanoate; t-amyl peroxyacetate; t-butyl peroxyacetate; t-butyl peroxybenzoate; OO-(t-amyl) O-(2-ethylhexyl)monoperoxycarbonate; OO-(t-butyl) O-isopropyl monoperoxycarbonate; OO-(t-butyl) O-(2-ethylhexyl) monoperoxycarbonate; polyether poly-t-butylperoxy carbonate; or t-butyl peroxy-3,5,5-trimethylhexanoate; or any combination thereof. Alternatively, the peroxide can include any combination of peroxides listed above.

The process chemistry supply system 130 can comprise a rinsing chemistry assembly (not shown) for providing rinsing chemistry for generating supercritical rinsing solutions within the processing chamber. The rinsing chemistry can include one or more organic solvents including, but not limited to, alcohols and ketones. For example, the rinsing chemistry can comprise solvents, such as N,N-dimethylacetamide (DMAc), gamma-butyrolactone (BLO), dimethyl sulfoxide (DMSO), ethylene carbonate (EC), N-methylpyrrolidone (NMP), dimethylpiperidone, propylene carbonate, and alcohols (such a methanol, ethanol and 2-propanol).

Moreover, the process chemistry supply system 130 can be configured to introduce treating chemistry for curing, cleaning, healing (or restoring the dielectric constant of low-k materials), or sealing, or any combination, low dielectric constant films (porous or non-porous). The chemistry can include hexamethyldisilazane (HMDS), chlorotrimethylsilane (TMCS), trichloromethylsilane (TCMS), dimethylsilyldiethylamine (DMSDEA), tetramethyldisilazane (TMDS), trimethylsilyldimethylamine (TMSDMA), dimethylsilyldimethylamine (DMSDMA), trimethylsilyldiethylamine (TMSDEA), bistrimethylsilyl urea (BTSU), bis(dimethylamino)methyl silane (B[DMA]MS), bis(dimethylamino)dimethyl silane (B[DMA]DS), HMCTS, dimethylaminopentamethyldisilane (DMAPMDS), dimethylaminodimethyldisilane (DMADMDS), disila-aza-cyclopentane (TDACP), disila-oza-cyclopentane (TDOCP), methyltrimethoxysilane (MTMOS), vinyltrimethoxysilane (VTMOS), or trimethylsilylimidazole (TMSI). Additionally, the chemistry may include N-tert-butyl-1,1-dimethyl-1-(2,3,4,5-tetramethyl-2,4-cyclopentadiene-1-yl)silanamine, 1,3-diphenyl-1,1,3,3-tetramethyidisilazane, or tert-butylchlorodiphenylsilane. For further details, see U.S. patent application Ser. No. 10/682,196, filed Oct. 10, 2003, and titled "METHOD AND SYSTEM FOR TREATING A DIELECTRIC FILM", and U.S. patent application Ser. No. 10/379,984, filed Mar. 4, 2003, and titled "METHOD OF PASSIVATING LOW DIELECTRIC MATERIALS IN WAFER PROCESSING", both incorporated by reference herein.

The processing system 100 can comprise a high-pressure fluid supply system 140. As shown in FIG. 1, the high-pressure fluid supply system 140 can be coupled to the recirculation system 120 using one or more lines 145, but this is not required. The inlet line 145 can be equipped with one or more back-flow valves, and/or heaters (not shown) for controlling the fluid flow from the high-pressure fluid supply system 140. In alternate embodiments, high-pressure fluid supply system 140 can be configured differently and coupled differently. For example, the high-pressure fluid supply system 140 can be coupled to the process module 110.

The high-pressure fluid supply system 140 can comprise a carbon dioxide source (not shown) and a plurality of flow control elements (not shown) for generating a supercritical fluid. For example, the carbon dioxide source can include a $CO_2$ feed system, and the flow control elements can include supply lines, valves, filters, pumps, and heaters. The high-pressure fluid supply system 140 can comprise an inlet valve (not shown) that is configured to open and close to allow or prevent the stream of supercritical carbon dioxide from flowing into the processing chamber 108. For example, controller 180 can be used to determine fluid parameters such as pressure, temperature, process time, and flow rate.

The processing system 100 can also comprise a pressure control system 160. As shown in FIG. 1, the pressure control system 160 can be coupled to the process module 110 using one or more lines 165, but this is not required. Line 165 can be equipped with one or more back-flow valves, pumps, and/or heaters (not shown) for controlling the fluid flow to pressure control system 160. In alternate embodiments, pressure control system 160 can be configured differently and coupled differently. For example, the pressure control system 160 can also include one or more pumps (not shown), and a sealing means (not shown) for sealing the processing chamber. In addition, the pressure control system 160 can comprise means for raising and lowering the substrate and/or the chuck.

In addition, the processing system 100 can comprise an exhaust control system 150. Alternately, an exhaust system may not be required. As shown in FIG. 1, the exhaust control system 150 can be coupled to the process module 110 using one or more lines 155, but this is not required. Line 155 can be equipped with one or more back-flow valves, and/or heaters (not shown) for controlling the fluid flow to the exhaust control system 150. In alternate embodiments, exhaust control system 150 can be configured differently and coupled differently. The exhaust control system 150 can include an exhaust gas collection vessel (not shown) and can be used to remove contaminants from the processing fluid. Alternately, the exhaust control system 150 can be used to recycle the processing fluid.

In one embodiment, controller 180 can comprise a processor 182 and a memory 184. Memory 184 can be coupled to processor 182, and can be used for storing information and instructions to be executed by processor 182. Alternately, different controller configurations can be used. In addition, controller 180 can comprise a port 185 that can be used to couple processing system 100 to another system (not shown). Furthermore, controller 180 can comprise input and/or output devices (not shown).

In addition, one or more of the processing elements (110, 120, 130, 140, 150,160, and 180) may include memory (not shown) for storing information and instructions to be executed during processing and processors for processing information and/or executing instructions. For example, the memory may be used for storing temporary variables or other intermediate information during the execution of instructions by the various processors in the system. One or more of the processing elements can comprise the means for reading data and/or instructions from a computer readable medium. In addition, one or more of the processing elements can comprise the means for writing data and/or instructions to a computer readable medium.

Memory devices can include at least one computer readable medium or memory for holding computer-executable instructions programmed according to the teachings of the invention and for containing data structures, tables, records, or other data described herein.

The processing system 100 can perform a portion or all of the processing steps of the invention in response to the controller 180 executing one or more sequences of one or more computer-executable instructions contained in a memory.

Such instructions may be received by the controller from another computer, a computer readable medium, or a network connection.

Stored on any one or on a combination of computer readable media, the present invention includes software for controlling the processing system 100, for driving a device or devices for implementing the invention, and for enabling the processing system 100 to interact with a human user and/or another system, such as a factory system. Such software may include, but is not limited to, device drivers, operating systems, development tools, and applications software. Such computer readable media further includes the computer program product of the present invention for performing all or a portion (if processing is distributed) of the processing performed in implementing the invention.

The term "computer readable medium" as used herein refers to any medium that participates in providing instructions to a processor for execution and/or that participates in storing information before, during, and/or after executing an instruction. A computer readable medium may take many forms, including but not limited to, non-volatile media, volatile media, and transmission media. The term "computer-executable instruction" as used herein refers to any computer code and/or software that can be executed by a processor, that provides instructions to a processor for execution and/or that participates in storing information before, during, and/or after executing an instruction.

Controller 180, processor 182, memory 184 and other processors and memory in other system elements as described thus far can, unless indicated otherwise below, be constituted by components known in the art or constructed according to principles known in the art. The computer readable medium and the computer executable instructions can also, unless indicated otherwise below, be constituted by components known in the art or constructed according to principles known in the art.

Controller 180 can use port 185 to obtain computer code and/or software from another system (not shown), such as a factory system. The computer code and/or software can be used to establish a control hierarchy. For example, the processing system 100 can operate independently, or can be controlled to some degree by a higher-level system (not shown).

The controller 180 can be coupled to the monitoring system 170 and data can be exchanged between the controller 180 and the monitoring system 170. The controller 180 can include means for determining a chemical composition of the processing fluid using data from the monitoring system 170, means for comparing the chemical composition to a threshold value, and means for altering the chemical composition of the processing fluid when the chemical composition is different than the threshold value. For example, additional fluid can be added to the recirculation loop when the chemical composition is greater than or equal to the threshold value, and additional process chemistry can be added to the recirculation loop when the chemical composition is less than the threshold value.

The controller 180 can use data from the monitoring system 170 to determine when to alter, pause, and/or stop a process. The controller 180 can use the data and operational rules to determine when to change a process and how to change the process, and rules can be used to specify the action taken for normal processing and the actions taken on exceptional conditions. Operational rules can be used to determine which processes are monitored and which data is used. For example, rules can be used to determine how to manage the data when a process is changed, paused, and/or stopped. In general, rules allow system and/or tool operation to change based on the dynamic state of the system.

Controller 180 can receive, send, use, and/or generate pre-process data, process data, and post-process data, and this data can include lot data, batch data, run data, composition data, and history data. Pre-process data can be associated with an incoming substrate and can be used to establish an input state for a substrate and/or a current state for a process module. Process data can include process parameters. Post processing data can be associated with a processed substrate and can be used to establish an output state for a substrate The controller 180 can use the pre-process data to predict, select, or calculate a process recipe to use to process the substrate. A process recipe can include a multi-step process involving a set of process modules. Post-process data can be obtained at some point after the substrate has been processed. For example, post-process data can be obtained after a time delay that can vary from minutes to days.

In one embodiment, the controller 180 can compute a predicted state for the chemical composition of the fluid based on the pre-process data, the process characteristics, and a process model. A process model can provide the relationship between one or more process recipe parameters or set points and one or more process results. The controller 180 can compare the predicted value to the measured value obtained from the monitoring system 170 to determine when to alter, pause, and/or stop a process.

In other embodiments, a reaction rate model can be used along with an expected contaminant level on the substrate to compute a predicted value for the chemical composition of the fluid, or a reaction rate model can be used along with a processing time to compute a predicted value for the chemical composition of the fluid.

In another embodiment, the controller 180 can use historical data and/or process models to compute an expected value for the chemical composition of the fluid at various times during the process. The controller 180 can compare the expected value to the measured value obtained from the monitoring system 170 to determine when to alter, pause, and/or stop a process.

In a supercritical cleaning/rinsing process, the desired process result can be a process result that is measurable using an optical measuring device, such as a Scanning Electron Microscopy (SEM). For example, the desired process result can be an amount of contaminant in a via or on the surface of a substrate. After one or more cleaning process run, the desired process can be measured.

It will be appreciated that the controller 180 can perform other functions in addition to those discussed here. The controller 180 can monitor variables associated with the other components in the processing system 100 and take actions based on these variables. For example, the controller 180 can process these variables, display these variables and/or results on a GUI screen, determine a fault condition, determine a response to a fault condition, and alert an operator.

In a supercritical cleaning/rinsing process, the desired process result can be a process result that is measurable using an optical measuring device, a Scanning Electron Microscopy (SEM), and/or Transmission Electron Microscopy (TEM). For example, the desired process result can be an amount of contaminant in a via or on the surface of a substrate. After one or more cleaning processes, the desired process result can be measured.

In addition, at least one of the processing elements (110, 120, 130, 140, 150, 160, 170, and 180) can comprise a GUI component and/or a database component (not shown). In alternate embodiments, the GUI component and/or the database component may not be required.

FIGS. 2A and 2B illustrate a simplified cross sectional view of a monitoring system in accordance with an embodiment of the invention. In the illustrated embodiment, a monitoring system 200 is shown that includes a holder 210 having a first section 202, a second section 204, and clamping means 206 for coupling the first section 202 to the second section 204. In alternate embodiments, other means such as screws (not shown) can be used to couple the first section 202 to the second section 204.

Although the clamping means 206 is shown in FIG. 2 as positioned near an outer edge of the holder 210, it is understood that the clamping means 206 can be configured and/or positioned in such a manner as to distribute pressure around the circumference and along a length of the holder 210 to optimize a seal between the holder 210 and a block of material 220. In an alternative embodiment, a number of clamping means may be used.

The monitoring system 200 can also include a block of material 220 coupled to the first section 202 and coupled to the second section 204. A first surface 222 of the block of material 220 can coupled to the first section 202 using a first sealing assembly 212, and a second surface 224 of the block of material 220 can coupled to the second section 204 using a second sealing assembly 214. In alternate embodiments, different configurations can be used for mounting blocks having different shapes in the holder. For example, one or more blocks of material may be used.

Furthermore, although the first section 202, the second section 204, and the clamping means 206 have been illustrated as single pieces, it is understood that the first section 202, the second section 204, and/or the clamping means 206 may comprise multiple pieces fitted together. In such an alternative configuration, additional seals and/or clamps can be used to ensure proper sealing. It is also understood that although single seals are shown additional seals can be used.

The block of material 220 can be substantially transparent to a light having a first set of wavelengths. In one embodiment, the block of material 220 can comprise calcium fluoride which is substantially transparent to infrared light. Calcium fluoride windows have previously been used in low pressure systems, but not in high pressure or supercritical processing systems. For example, a calcium fluoride window can provide a greater than 90% transmission of light with wavelength between 250 nm and 7 um. Calcium fluoride is commercially available in prefabricated forms, such as square or rectangular blocks, or as disks with a consistent thickness, and in various dimensions.

Referring again to FIG. 2A, the monitoring system 200 includes a input port 230, a first connecting element 235 for coupling the input port 230 to a first fluid line (172 FIG. 1) in the recirculation loop, output port 240, and a second connecting element 245 for coupling the output port 240 to a second fluid line (174 FIG. 1) in the recirculation loop. In addition, a passageway 255 through the monitoring system includes the input port 230, a fluid passage 203 in the first section 202, a fluid passage 223 in the block of material 220, a fluid passage 205 in the second section 204, and the output port 240.

In addition, a first sealing means 236 and a first hardware means 237 can be included for coupling the first connecting element 235 to the first section 202, and a second sealing means 246 and a second hardware means 247 can be included for coupling the second connecting element 245 to the second section 204. A mounting surface of the first section 202 can be configured to match the dimensions of the first connecting element 235. The first sealing means 236 can be positioned between the first section 202 and the first connecting element 235. The first sealing means 236 surrounds the fluid passage 255 to prevent leaking of any processing fluid passing through the fluid passage 255. In a similar manner, a mounting surface of the second section 204 can be configured to match the dimensions of the second connecting element 245. The second sealing means 246 can be positioned between the second section 204 and the second connecting element 245. The second sealing means 246 surrounds the fluid passage 255 to prevent leaking of any processing fluid passing through the fluid passage 255. The first sealing means 236 and the second sealing means 246 can comprise o-rings. The first and the second hardware means can be configured and/or positioned in such a manner as to more evenly distribute pressure across the mounting surfaces. Application of such pressure also ensures optimal sealing by the first sealing means 236 and the second sealing means 246. It is also understood that more or less hardware can be used than shown in FIG.2.

The monitoring system 200 further comprises transmission window 250 and a reception window 250 configured on opposite sides of the block of material 220. For example, an optical source (not shown) for creating a light beam can be coupled to the transmission window 250, and an optical detector (not shown) for receiving the light beam can be coupled to a reception window 260; a light beam can be passed through the block of material 220 for monitoring the flow of the high-pressure processing fluid through the flow passage 255. In an alternate embodiment, a transmission window 250 and a reception window 260 are not required, but a means for mounting an optical source and a means for mounting an optical detector may be provided. It is well known that an optical source and/or optical detector can comprise a connecting means (not shown) that can be used to send and/or receive signals from a controller (not shown).

In FIGS. 2A and 2B, a cylindrical shape elements are shown, but this is not required for the invention. In alternate embodiments, non-cylindrical shapes may be used for the holder and/or the block of material. In addition, the diameter of the block of material 220 is shown to be less than the diameter of the holder 210, but this is not required for the invention. Alternately, the diameter of the block of material 220 may be approximately equal to the diameter of the holder 210. Furthermore, the diameter of a hole 320 (FIG. 3A) through the block of material 220 is equal to the diameter of the fluid passages 203 and 205 and the inside diameter of the input port 230 and output port 240. For example, a constant diameter passage 255 can be provided through the monitoring system 200.

A contact surface of the first section 202, can be configured to match the dimensions of the first surface 222. In this manner, pressure applied by the first section 202 is evenly distributed across the entire first surface 222. A first sealing assembly 212 can be positioned between the first section 202 and the first surface 222. The first sealing assembly 212 preferably surrounds the hole 320 to prevent leaking of any solution passing through the hole 320. In a similar manner, a contact surface of the second section 204 can be configured to match the dimensions of the second surface 224. In this manner, pressure applied by the second section 204 can be evenly distributed across the entire second surface 224. A second sealing assembly 214 can be positioned between the second section 204 and the second surface 224. The second sealing assembly 214 preferably surrounds the hole 320 to prevent leaking of any solution passing through the hole 320. The first sealing assembly 212 and the second sealing assembly 214 can comprise o-rings. Alternatively, any other conventional pressure sealing means sufficient to prevent solution from leaking can be used.

In alternate embodiments, the monitoring system 200 may comprise a heater, a temperature sensor, a pressure sensor, and/or a flow sensor.

Figure 3A:
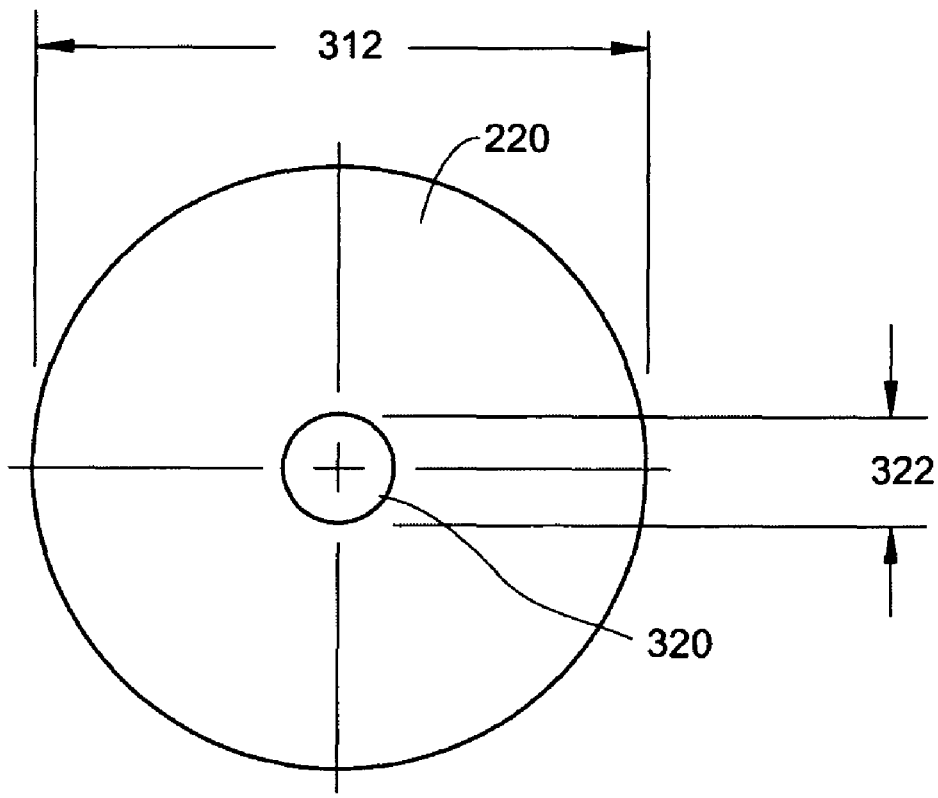
FIGS. 3A and 3B illustrate a simplified view of a block of material in accordance with embodiments of the invention.
Figure 3B:
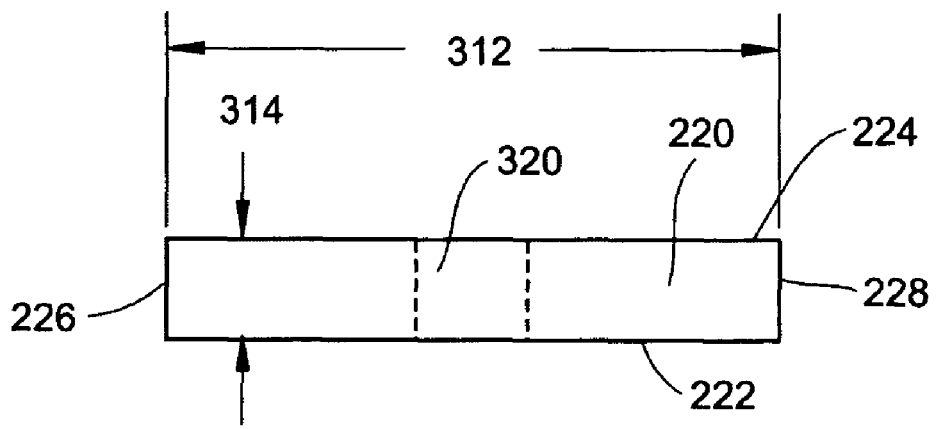

FIGS. 3A and 3B illustrate a simplified view of a block of material in accordance with embodiments of the invention. As shown, the block of material 220 can have a disk shape (annular ring) with a diameter 312 (FIG. 3A) and a thickness 314 (FIG. 3B). For example, a disk shaped calcium fluoride window can be manufactured from a preformed calcium fluoride block, such as a cylindrical or rectangular block, or from a preformed calcium fluoride disk, which are commercially available. Calcium fluoride disks are commercially available as preformed rectangular blocks with length and width of approximately one-half inch and thickness or approximately five millimeters. Calcium fluoride disks are commercially available as preformed disks with diameter of approximately one-half inch and thickness of approximately five millimeters. It is well known in the art that preformed calcium fluoride windows of other dimensions are also available.

FIG. 3A illustrates a top down view of the block of material 220. The block of material 220 includes a disk shape with diameter 312. A hole 320 is provided through the block of material 220. The hole 320 can be located in the center of the block of material 220 and can have a diameter 322. FIG. 3B illustrates a side view of the block of material 220. The block of material 220 comprises a thickness 314.

The block of material 220 can includes a first surface 222 and a second surface 224. The thickness (314 FIG. 3B) can be measured as the distance from the first surface 222 to the second surface 224. The block of material 220 can also include a first side 226 and a second side 228. Although the preferred configuration of the material block 220 is a disk, and as such does not include "sides", the reference to first side 226 and second side 228 is used to define relative end points on the diameter 312 along the circumference of the disk shaped block of material 220.

In one embodiment, an infrared light beam passes through the diameter of the calcium fluoride disk in order to examine a stream of processing fluid within a recirculation loop that operates at supercritical pressures during one or more steps in a process. Processing fluid that contains carbon dioxide and/or process chemistry passes through a hole in the calcium fluoride disk and the chemical composition is measured using the infrared light beam. The optical components can be outside the high pressure environment, and the calcium fluoride disk contains the high pressure processing fluid. Such a configuration enables an infrared light beam to access the high pressure processing fluid and then to exit for analysis.

In an alternate embodiment, the block of material 220 is replaced by two or more pieces of block material, such as pieces of calcium fluoride. For example, one piece can be used as a transmission window and another piece may be used as a reception window. Hardware may be adapted to secure the calcium fluoride pieces into place and to prevent leaking of the processing fluid.

FIGS. 4A and 4B illustrate a simplified cross sectional view of another monitoring system in accordance with the invention. In the illustrated embodiment, a monitoring system 400 is shown that includes a holder 410 having a first section 402, a second section 404, and clamping means 406 for coupling the first section 402 to the second section 404. In alternate embodiments, other means such as screws (not shown) can be used to couple the first section 402 to the second section 404.

Although the clamping means 406 is shown in FIG. 4 as positioned near an outer edge or the holder 410, it is understood that the clamping means 406 can be configured and/or positioned in such a manner as to distribute pressure around the outer faces and along a length of the holder 410 to optimize a seal between the holder 410 and the block of material 420. In an alternative embodiment, a number of clamping means may be used.

The monitoring system 400 can also include a block of material 420 coupled to the first section 402 and coupled to the second section 404. A first surface 422 of the block of material 420 can coupled to the first section 402 using a first sealing assembly 412, and a second surface 424 of the block of material 420 can coupled to the second section 404 using a second sealing assembly 414. In alternate embodiments, different configurations can be used for mounting blocks having different shapes in the holder. For example, one or more blocks of material may be used.

Furthermore, although the first section 402, the second section 404, and the clamping means 406 have been illustrated as single pieces, it is understood that the first section 402, the second section 404, and/or the clamping means 406 may comprise multiple pieces fifted together. In such an alternative configuration, additional seals and/or clamps can be used to ensure proper sealing. It is also understood that although single seals are shown additional seals can be used.

The block of material 420 can be substantially transparent to a light having a first set of wavelengths. In one embodiment, the block of material 420 can comprise calcium fluoride, which is substantially transparent to infrared light. Calcium fluoride windows have previously been used in low pressure systems, but not in high pressure or supercritical processing systems. For example, a calcium fluoride window can provide a greater than 90% transmission of light with wavelength between 450 nm and 7 um. Calcium fluoride is commercially available in prefabricated forms, such as square or rectangular blocks, or as slabs with a consistent thickness, and in various dimensions.

Referring again to FIG. 4A, the monitoring system 400 includes a input port 430, a first connecting element 435 for coupling the input port 430 to a first fluid line (172 FIG. 1) in the recirculation loop, output port 440, and a second connecting element 445 for coupling the output port 440 to a second fluid line (174 FIG. 1) in the recirculation loop. In addition, a passageway 455 through the monitoring system 400 includes the input port 430, a fluid passage 403 in the first section 402, a fluid passage 423 in the block of material 420, a fluid passage 405 in the second section 404, and the output port 440.

In addition, a first sealing means 436 and a first hardware means 437 can be included for coupling the first connecting element 435 to the first section 402, and a second sealing means 446 and a second hardware means 447 can be included for coupling the second connecting element 445 to the second section 404. A mounting surface of the first section 402 can be configured to match the dimensions of the first connecting element 435. The first sealing means 436 can be positioned between the first section 402 and the first connecting element 435. The first sealing means 436 surrounds the fluid passage 455 to prevent leaking of any processing fluid passing through the fluid passage 455. In a similar manner, a mounting surface of the second section 404 can be configured to match the dimensions of the second connecting element 445. The second sealing means 446 can be positioned between the second section 404 and the second connecting element 445. The second sealing means 446 surrounds the fluid passage 455 to prevent leaking of any processing fluid passing through the fluid passage 455. The first sealing means 436 and the second sealing means 446 can comprise o-rings. The first and the second hardware means can be configured and/or positioned in such a manner as to more evenly distribute pressure across the mounting surfaces. Application of such pressure also ensures optimal sealing by the first sealing means 436 and the second sealing means 446. It is also understood that more or less hardware can be used than shown in FIG. 4A.

The monitoring system 400 further comprises transmission window 450 and a reception window 460 configured on opposite sides of the block of material 420. For example, an optical source (not shown) for creating a light beam can be coupled to the transmission window 450, and an optical detector (not shown) for receiving the light beam can be coupled to the reception window 460; a light beam can be passed through the block of material 420 for monitoring the flow of the high-pressure processing fluid through the flow passage 455. In an alternate embodiment, a transmission window 450 and a reception window 460 are not required, but a means for mounting an optical source and a means for mounting an optical detector may be provided. It is well known that an optical source and/or optical detector can comprise a connecting means (not shown) that can be used to send and/or receive signals from a controller (not shown).

In FIGS. 4A and 4B, rectangular shaped elements are shown, but this is not required for the invention. In alternate embodiments, square shapes may be used for the holder and/or the block of material. In addition, the surface area of the block of material 420 is shown to be less than the surface area of the holder 410, but this is not required for the invention. Alternately, the surface area of the block of material 420 may be approximately equal to the surface area of the holder 410. Furthermore, the diameter of the hole 520 (FIG. 5A) through the block of material 420 is equal to the diameter of the fluid passages 403 and 405 and the inside diameter of the input port 430 and output port 440. For example, a constant diameter passage 455 can be provided through the monitoring system 400.

A contact surface of the first section 402, can be configured to match the dimensions of the first surface 422. In this manner, pressure applied by the first section 402 is evenly distributed across the entire first surface 422. A first sealing assembly 412 can be positioned between the first section 402 and the first surface 422. The first sealing assembly 412 preferably surrounds the hole 520 to prevent leaking of any solution passing through the hole 520. In a similar manner, a contact surface of the second section 404 can be configured to match the dimensions of the second surface 424. In this manner, pressure applied by the second section 404 can be evenly distributed across the entire second surface 424. A second sealing assembly 414 can be positioned between the second section 404 and the second surface 424. The second sealing assembly 414 preferably surrounds the hole 520 to prevent leaking of any solution passing through the hole 520. The first sealing assembly 412 and the second sealing assembly 414 can comprise o-rings. Alternatively, any other conventional pressure sealing means sufficient to prevent solution from leaking can be used.

In alternate embodiments, the monitoring system 400 may comprise a heater, a temperature sensor, a pressure sensor, and/or a flow sensor.

Figure 5A:
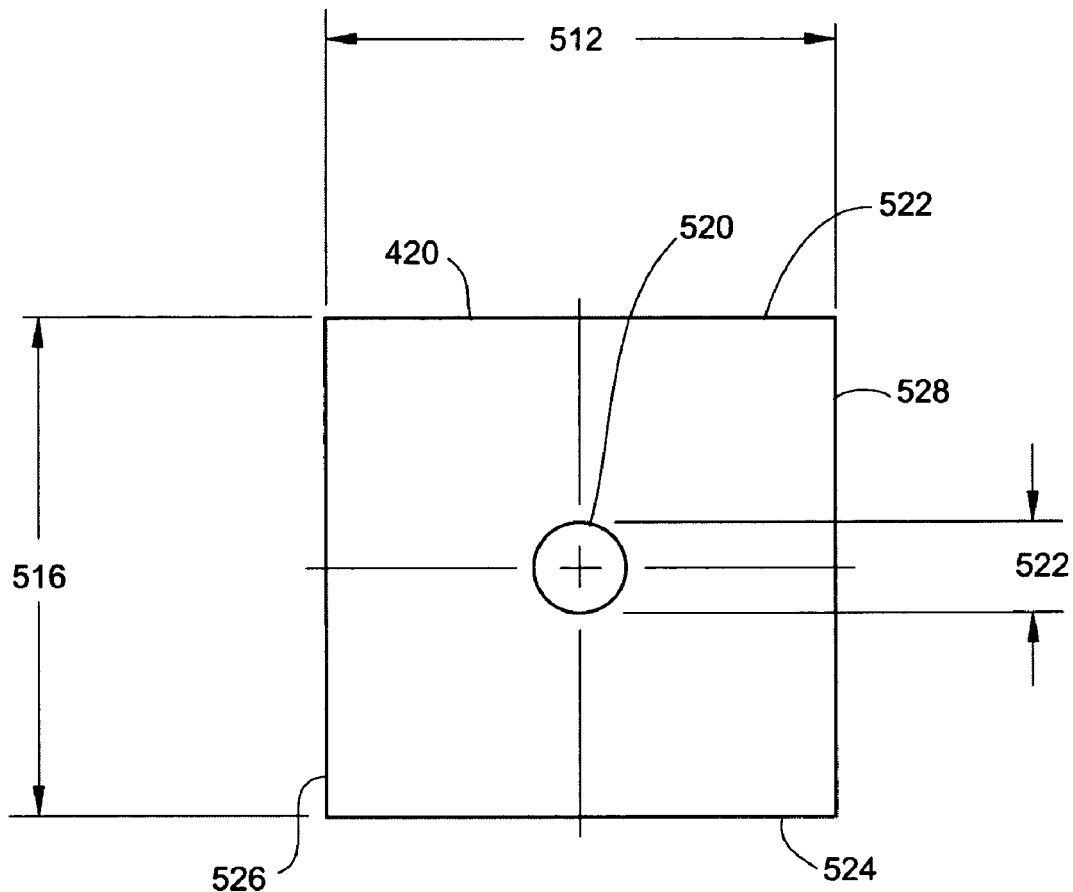
FIGS. 5A and 5B illustrate a simplified view of another block of material in accordance with embodiments of the invention.
Figure 5B:
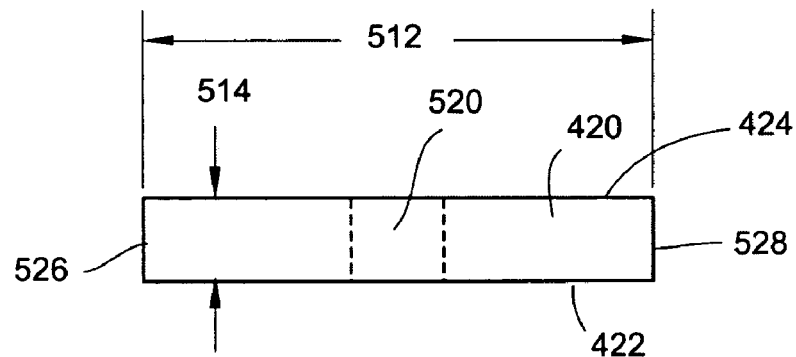

FIGS. 5A and 5B illustrate a simplified view of another block of material in accordance with embodiments of the invention. In the illustrated embodiment, a block of material 420 having a square shape with a length 512 (FIG. 5A), a width 516 (FIG. 5A), and a thickness 514 (FIG. 5B). Alternately, other shapes may be used. For example, a square or rectangular shaped calcium fluoride window can be manufactured from a preformed calcium fluoride block, such as a square or rectangular block, or from a preformed calcium fluoride disk, which are commercially available. Calcium fluoride disks are commercially available as preformed rectangular blocks with length and width of approximately one-half inch and thickness or approximately five millimeters. Calcium fluoride disks are commercially available as preformed disks with diameter of approximately one-half inch and thickness of approximately five millimeters. It is well known in the art that preformed calcium fluoride windows of other dimensions are also available.

FIG. 5A illustrates a top down view of the block of material 420. The block of material 420 can have a uniform thickness 514 and a hole 520 can be provided through the block of material 420. The hole 520 can be located in the center of the block of material 420 and can have a diameter 522. FIG. 5B illustrates a side view of the block of material 420. Alternately, the block of material 420 may have a non-uniform thickness.

The block of material 420 can include a first surface 422 and a second surface 424. The thickness (514 FIG. 5B) can be measured as the distance from the first surface 422 to the second surface 424. The block of material 420 can also include a first side 522, a second side 524, a third side 526, and a fourth side 528. In one example, an infrared light beam may be passed from one side to another side of the block through the hole in order to examine a stream of processing fluid within a recirculation loop that operates at supercritical pressures during one or more steps in a process. When processing fluid that contains carbon dioxide and/or process chemistry passes through a hole in the calcium fluoride block, the chemical composition can be measured using the infrared light beam. The optical components can be coupled to one or more sides of the block and remain outside the high pressure environment. The calcium fluoride block can contain the high pressure processing fluid. Such a configuration enables an infrared light beam to access the high pressure processing fluid and then to exit for analysis.

In an alternate embodiment, the block of material 420 may be replaced by two or more pieces of block material, such as pieces of calcium fluoride. For example, one piece can be used as a transmission window and another piece may be used as a reception window. Hardware may be adapted to secure the calcium fluoride pieces into place and to prevent leaking of the processing fluid.

During substrate processing, providing processing fluids that are contaminated or contain an incorrect chemical composition can have a negative affect on the process. For example, an incorrect processing fluid can affect the process chemistry, process dropout, and process uniformity. In another embodiment, monitoring system may be used during a maintenance or system cleaning operation in which cleaning chemistry is used to remove process by-products and/or particles from the interior surfaces of the system. This is a preventative maintenance operation in which maintaining low contaminant levels and correct temperatures prevents material from adhering to the interior surfaces of the system that can be dislodged later during processing and that can cause unwanted particle deposition on a substrate. The transmission factor for the monitoring system can be monitored during processing and/or during cleaning to determine if the transmission and reception windows are clean or coated.

Figure 6:
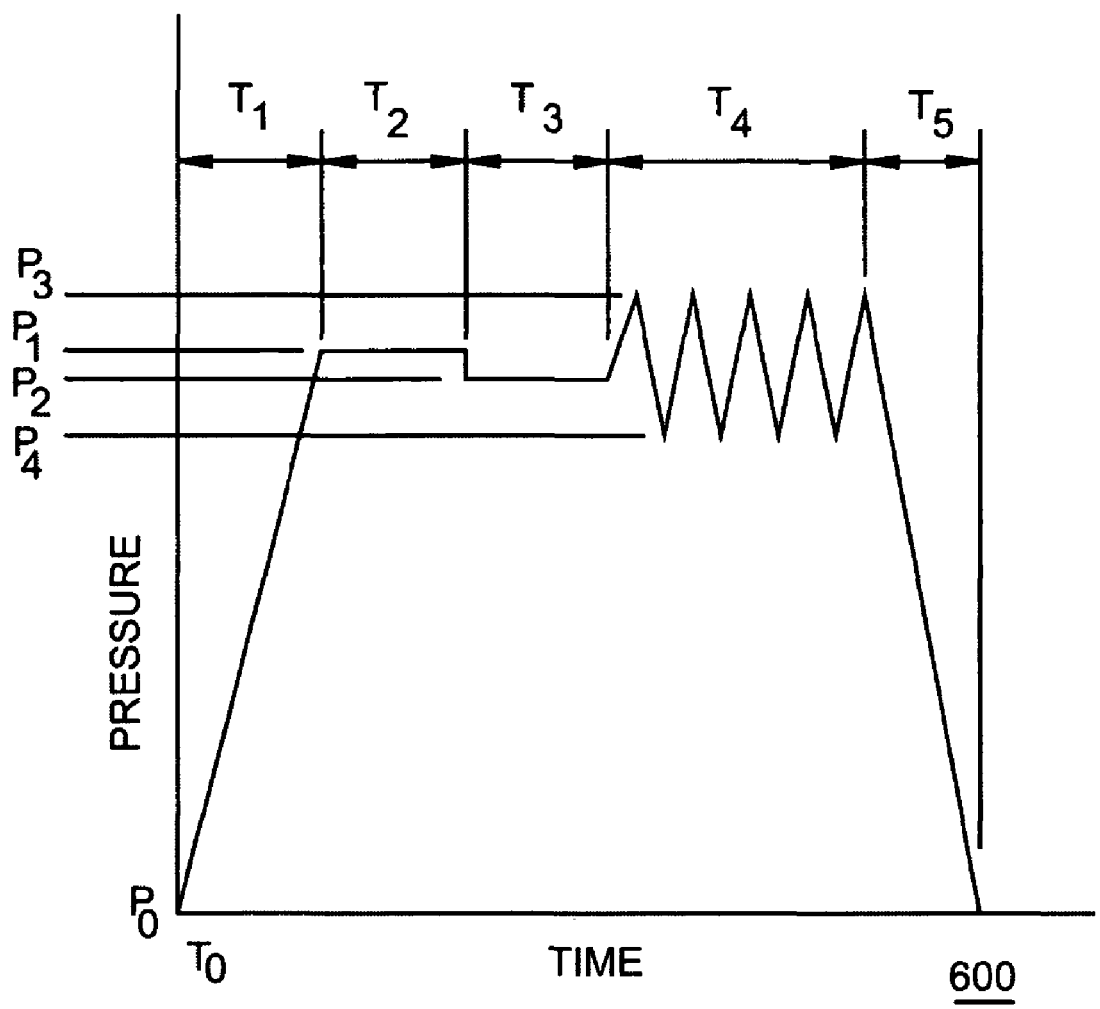
FIG. 6 illustrates an exemplary graph of pressure versus time for supercritical processes in accordance with an embodiment of the invention.

FIG. 6 illustrates an exemplary graph of pressure versus time for a supercritical process step in accordance with embodiments of the invention. In the illustrated embodiment, a graph 600 of pressure versus time is shown, and the graph 600 can be used to represent a supercritical cleaning process step, a supercritical rinsing process step, or a supercritical curing process step, or a combination thereof. Alternately, different pressures, different timing, and different sequences may be used for different processes. In addition, although a single time sequence is illustrated in FIG. 6, this is not required for the invention. Alternately, multi-sequence processes may be used.

Referring to both FIGS. 1 and 6, prior to an initial time To, the substrate to be processed can be placed within the processing chamber 108 and the processing chamber can be sealed. For example, during cleaning, rinsing, and/or curing processes, a substrate can have post-etch and/or post-ash residue thereon. The substrate, the processing chamber, and the other elements in the recirculation loop 115 can be heated to an operational temperature. For example, the operational temperature can range from 40 to 300 degrees Celsius.

During time $T_1$, the processing chamber 108 and the other elements in the recirculation loop 115 can be pressurized. During at least one portion of the time $T_1$, the high-pressure fluid supply system 140 can be coupled into the flow path and can be used to provide temperature controlled carbon dioxide into the processing chamber and/or other elements in the recirculation loop 115. For example, the temperature variation of the temperature-controlled carbon dioxide can be controlled to be less than approximately ten degrees Celsius during the pressurization process.

In one embodiment, the monitoring system 170 can operate during the first portion of the time $T_1$ and can provide baseline data. Alternately, the monitoring system may not be operated during the first portion of the time $T_1$.

During time $T_1$, a pump (not shown) in the recirculation system 120 can be started and can be used to circulate the temperature controlled fluid through the monitoring system, the processing chamber, and the other elements in the recirculation loop. In one embodiment, the monitoring system 170 can operate while the fluid is being circulated and can provide a first set of operational data. Alternately, the monitoring system may not be operated during this portion of the time $T_1$.

In one embodiment, when the pressure in the processing chamber 108 exceeds a critical pressure Pc (1,070 psi), process chemistry can be injected into the recirculation loop 115 using the process chemistry supply system 130. In one embodiment, the high-pressure fluid supply system 140 can be switched off before the process chemistry is injected. Alternately, the high-pressure fluid supply system 140 can be switched on while the process chemistry is injected.

In other embodiments, process chemistry may be injected into the processing chamber 108 before the pressure exceeds the critical pressure Pc (1,070 psi) using the process chemistry supply system 130. For example, the injection(s) of the process chemistries can begin upon reaching about 1100-1200 psi. In other embodiments, process chemistry is not injected during the $T_1$ period.

In addition, the monitoring system 170 can operate before, during, and/or after the process chemistry is injected. The monitoring system can be used to control the injection process. Process chemistry can be injected in a linear fashion, and the injection time can be based on a recirculation time. For example, the recirculation time can be determined based on the length of the recirculation path and the flow rate. In other embodiments, process chemistry may be injected in a non-linear fashion. For example, process chemistry can be injected in one or more steps.

The process chemistry can include a cleaning agent, a rinsing agent, or a curing agent, or a combination thereof that is injected into the supercritical fluid. One or more injections of process chemistries can be performed over the duration of time $T_1$ to generate a supercritical processing solution with the desired concentrations of chemicals. The process chemistry, in accordance with the embodiments of the invention, can also include one more or more carrier solvents.

Still referring to both FIGS. 1, and 6, during a second time $T_2$, the supercritical processing solution can be re-circulated over the substrate and through the monitoring system 170, the processing chamber 108, and the other elements in the recirculation loop 115.

In one embodiment, the monitoring system 170 (FIG. 1) can operate while the supercritical processing solution is being re-circulated. Alternately, the monitoring system may not be operated while the supercritical processing solution is being re-circulated. The monitoring system can be used to control the chemical composition while the supercritical processing solution is being re-circulated. For example, the high-pressure fluid supply system 140 can be switched off, and process chemistry not injected during the second time $T_2$. Alternatively, the high-pressure fluid supply system 140 can be switched on, and process chemistry may be injected into the processing chamber 108 during the second time $T_2$ or after the second time $T_2$.

The processing chamber 108 can operate at a pressure $P_1$ above 1,500 psi during the second time $T_2$. For example, the pressure can range from approximately 2,500 psi to approximately 3,100 psi, but can be any value so long as the operating pressure is sufficient to maintain supercritical conditions. The supercritical processing solution can be circulated over the substrate and through the recirculation loop 115. The super-critical conditions within the processing chamber 108 and the other elements in the recirculation loop 115 are maintained during the second time $T_2$, and the supercritical processing solution continues to be circulated over the substrate and through the processing chamber 108 and the other elements in the recirculation loop 115. The recirculation system 120 can be used to regulate the flow of the supercritical processing solution through the processing chamber 108 and the other elements in the recirculation loop 115.

Still referring to both FIGS. 1 and 6, during a third time $T_3$, one or more push-through processes can be performed. The high-pressure fluid supply system 140 can comprise means for providing a first volume of temperature-controlled fluid during a push-through process, and the first volume can be larger than the volume of the recirculation loop. Alternately, the first volume can be less than or approximately equal to the volume of the recirculation loop. In addition, the temperature differential within the first volume of temperature-controlled fluid during the push-through process can be controlled to be less than approximately ten degrees Celsius.

In one embodiment, the monitoring system 170 can operate during a push-through process. Alternately, the monitoring system may not be operated during a push-through process. The monitoring system can be used to control the chemical composition during a push-through process. For example, during the third time $T_3$, one or more volumes of temperature controlled supercritical carbon dioxide can be fed into the recirculation loop 115 from the high-pressure fluid supply system 140, and the supercritical processing solution along with process residue suspended or dissolved therein can be displaced from the processing chamber 108 and the other elements in the recirculation loop 115 through the exhaust control system 150. The monitoring system can be used to measure the process residue in the processing solution. Providing temperature-controlled fluid during the push-through process prevents process residue suspended or dissolved within the fluid being displaced from the processing chamber 108 and the other elements in the recirculation loop 115 from dropping out and/or adhering to the processing chamber 108 and the other elements in the recirculation loop 115. In addition, during the third time $T_3$, the temperature of the fluid supplied by the high-pressure fluid supply system 140 can vary over a wider temperature range than the range used during the second time $T_2$.

In the illustrated embodiment shown in FIG. 6, a single second time $T_2$ is followed by a single third time $T_3$, but this is not required. In alternate embodiments, other time sequences may-be used to process a substrate. In addition, during the second time $T_2$, the pressure $P_1$ can be higher than the pressure $P_2$ during the third time $T_3$. Alternatively, $P_1$ and $P_2$ may have different values.

After the push-through process is complete, a pressure cycling process can be performed. Alternately, one or more pressure cycles can occur during the push-through process. In other embodiments, a pressure cycling process is not required. During a fourth time $T_4$, the processing chamber 108 can be cycled through a plurality of decompression and compression cycles. The pressure can be cycled between a first pressure $P_3$ and a second pressure $P_4$ one or more times. In alternate embodiments, the first pressure $P_3$ and a second pressure $P_4$ can vary. In one embodiment, the pressure can be lowered by venting through the exhaust control system 150. For example, this can be accomplished by lowering the pressure to below approximately 1,500 psi and raising the pressure to above approximately 2,500 psi. The pressure can be increased by using the high-pressure fluid supply system 140 to provide additional high-pressure fluid.

The high-pressure fluid supply system can comprise means for providing a first volume of temperature-controlled fluid during a compression cycle, and the first volume can be larger than the volume of the recirculation loop. Alternatively, the first volume can be less than or approximately equal to the volume of the recirculation loop. In addition, the temperature differential within the first volume of temperature-controlled fluid during the compression cycle can be controlled to be less than approximately ten degrees Celsius. In addition, the high-pressure fluid supply system can comprise means for providing a second volume of temperature-controlled fluid during a decompression cycle, and the second volume can be larger than the volume of the recirculation loop. Alternatively, the second volume can be less than or approximately equal to the volume of the recirculation loop. In addition, the temperature differential within the second volume of temperature-controlled fluid during the decompression cycle can be controlled to be less than approximately ten degrees Celsius. Alternatively, the temperature variation of the temperature-controlled fluid can be controlled to be less than approximately five degrees Celsius during a decompression cycle.

In one embodiment, the monitoring system 170 can operate during a pressure cycling process. Alternatively, the monitoring system may not be operated during a pressure cycling process. The monitoring system can be used to control the chemical composition during a pressure cycling process. For example, during the fourth time $T_4$, one or more volumes of temperature controlled supercritical carbon dioxide can be fed into the processing chamber 108 and the other elements in the recirculation loop 115 from the high-pressure fluid supply system 140, and the supercritical processing solution along with process residue suspended or dissolved therein can be displaced from the processing chamber 108 and the other elements in the recirculation loop 115 through the exhaust control system 150. The monitoring system can be used to measure the process residue in the processing solution before, during, and/or after a pressure cycling process.

Providing temperature-controlled fluid during the pressure cycling process prevents process residue suspended or dissolved within the fluid being displaced from the processing chamber 108 and the other elements in the recirculation loop 115 from dropping out and/or adhering to the processing chamber 108 and the other elements in the recirculation loop 115. In addition, during the fourth time $T_4$, the temperature of the fluid supplied by the high-pressure fluid supply system 140 can vary over a wider temperature range than the range used during the second time $T_2$.

In the illustrated embodiment shown in FIG. 6, a single third time $T_3$ is followed by a single fourth time $T_4$, but this is not required. In alternate embodiments, other time sequences may be used to process a substrate.

In an alternate embodiment, the high-pressure fluid supply system 140 can be switched off during a portion of the fourth time $T_4$. For example, the high-pressure fluid supply system 140 can be switched off during a decompression cycle.

During a fifth time $T_5$, the processing chamber 108 can be returned to lower pressure. For example, after the pressure cycling process is completed, then the processing chamber can be vented or exhausted to a pressure compatible with a transfer system In one embodiment, the monitoring system 170 (FIG. 1) can operate during a venting process. Alternately, the monitoring system may not be operated during a venting process. The monitoring system can be used to control the chemical composition during a venting process. The high-pressure fluid supply system 140 can comprise means for providing a volume of temperature-controlled fluid during a venting process, and the volume can be larger than the volume of the recirculation loop. Alternatively, the volume can be less than or approximately equal to the volume of the recirculation loop. For example, during the fifth time $T_5$, one or more volumes of temperature controlled supercritical carbon dioxide can be fed into the processing chamber 108 and the other elements in the recirculation loop 115 from the high-pressure fluid supply system 140, and the remaining processing solution along with process residue suspended or dissolved therein can be displaced from the processing chamber 108 and the other elements in the recirculation loop 115 through the exhaust control system 150. The monitoring system can be used to measure the process residue in the processing solution before, during, and/or after a venting process.

In the illustrated embodiment shown in FIG. 6, a single fourth time $T_4$ is followed by a single fifth time $T_5$, but this is not required. In alternate embodiments, other time sequences may be used to process a substrate.

In one embodiment, during a portion of the fifth time $T_5$, the high-pressure fluid supply system 140 can be switched off. In addition, the temperature of the fluid supplied by the high-pressure fluid supply system 140 can vary over a wider temperature range than the range used during the second time $T_2$. For example, the temperature can range below the temperature required for supercritical operation.

For substrate processing, the chamber pressure can be made substantially equal to the pressure inside of a transfer chamber (not shown) coupled to the processing chamber. In one embodiment, the substrate can be moved from the processing chamber into the transfer chamber, and moved to a second process apparatus or module to continue processing.

In the illustrated embodiment shown in FIG. 6, the pressure returns to an initial pressure $P_0$, but this is not required for the invention. In alternate embodiments, the pressure does not have to return to $P_0$, and the process sequence can continue with additional time steps such as those shown in time steps $T_1$, $T_2$, $T_3$, $T_4$, or $T_5$ The graph 600 is provided for exemplary purposes only. It will be understood by those skilled in the art that a supercritical processing step can have any number of different time/pressures or temperature profiles without departing from the scope of the invention. Further, any number of cleaning, rinsing, and/or curing process sequences with each step having any number of compression and decompression cycles are contemplated. In addition, as stated previously, concentrations of various chemicals and species within a supercritical processing solution can be readily tailored for the application at hand and altered at any time within a supercritical processing step.

Figure 7:
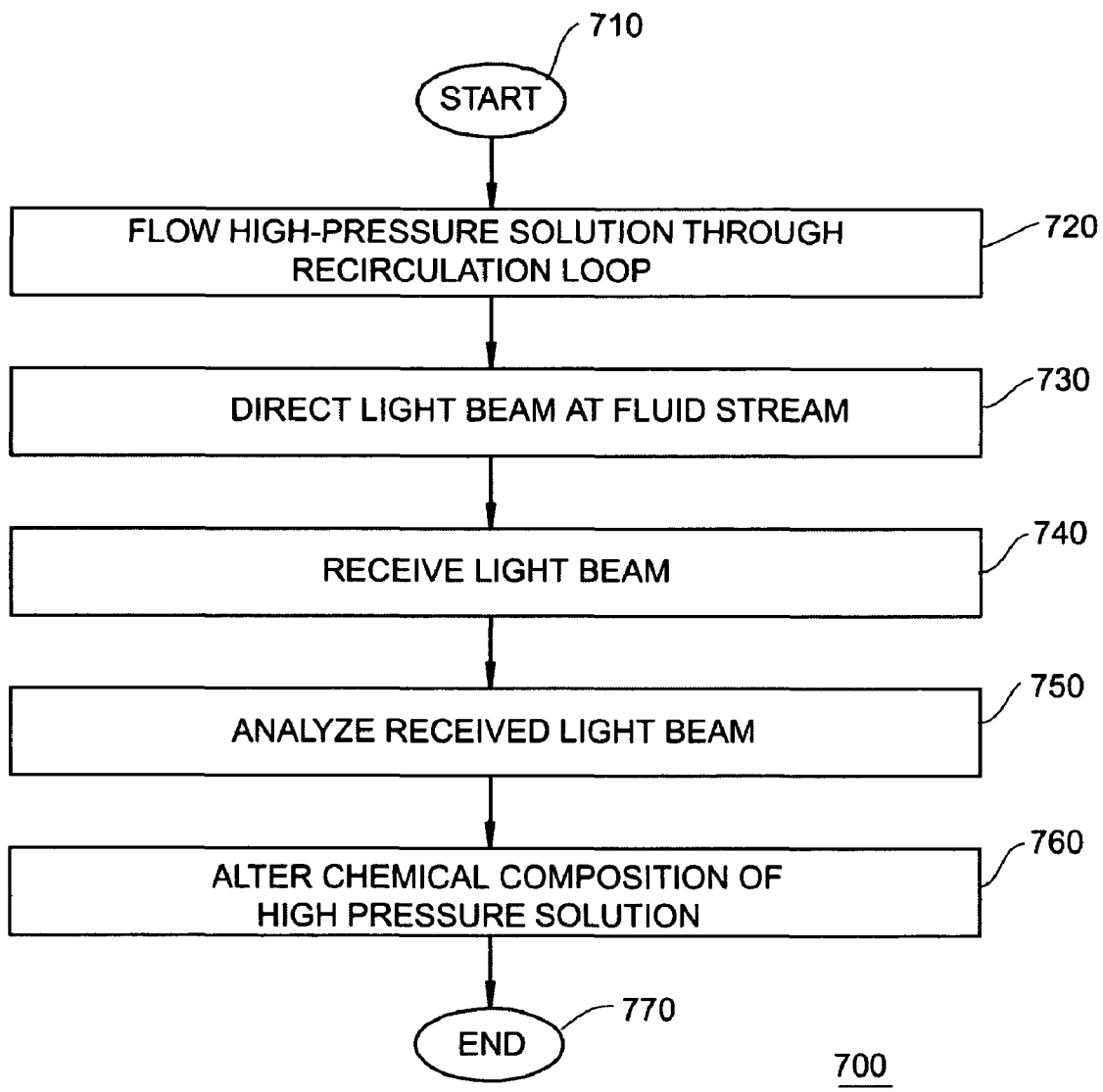
FIG. 7 illustrates a method of analyzing a high-pressure solution within a closed loop environment in accordance with an embodiment of the invention.

FIG. 7 illustrates a flow diagram of a method for monitoring a high-pressure processing fluid flowing through a recirculation loop in a high-pressure processing system in accordance with an embodiment of the invention. Procedure 700 starts in 710 wherein a substrate can be positioned within a processing chamber that is part of the recirculation loop.

In 720, a high pressure solution can flow through the recirculation loop, the recirculation loop including a monitoring system through which the high-pressure processing fluid passes, the monitoring system including a block material that is substantially transparent to an infrared light beam.

In 730, an infrared light beam can be directed at a first side of the block material such that the infrared light beam passes through the block material and the high-pressure processing fluid passing therethrough.

In 740, the infrared light beam exiting from a second side of the block material can be received.

In 750, the received infrared light beam can be analyzed to determine the chemical composition of the high-pressure processing fluid. Fourier transform techniques can be used in the analysis.

In 760, the composition of the processing fluid is altered based on the chemical composition of the high-pressure processing fluid.

Procedure 700 can end in 770.

While the invention has been described in terms of specific embodiments incorporating details to facilitate the understanding of the principles of construction and operation of the invention, such reference herein to specific embodiments and details thereof is not intended to limit the scope of the claims appended hereto. It will be apparent to those skilled in the art that modifications may be made in the embodiments chosen for illustration without departing from the spirit and scope of the invention.

What is claimed is:

1. A system for monitoring a processing fluid within a high-pressure processing system, the system comprising:
 a recirculation loop comprising a high pressure processing chamber and a high pressure recirculation system coupled to the high pressure processing chamber, wherein the processing fluid flows through the recirculation loop;
 a high-pressure fluid supply system coupled to the recirculation loop and comprising means for supplying fluid to the recirculation loop;
 a process chemistry supply system coupled to the recirculation loop and comprising means for supplying process chemistry to the recirculation loop;
 a pressure control system coupled to the recirculation loop;
 an exhaust system coupled to the recirculation loop;
 a monitoring system coupled to the recirculation loop for monitoring the processing fluid flowing through the recirculation loop; and
 a controller coupled to the high pressure processing chamber, the recirculation system, the high-pressure fluid supply system, the process chemistry supply system, the pressure control system, the exhaust system, and the monitoring system wherein the controller comprises means for determining a chemical composition of the processing fluid using data from the monitoring system, means for comparing the chemical composition to a threshold value, means for providing additional fluid to the recirculation loop when the chemical composition is greater than or equal to the threshold value, and means for providing additional process chemistry to the recirculation loop when the chemical composition is less than the threshold value.

2. The system as claimed in claim 1, wherein the monitoring system comprises an optical monitor coupled to the recirculation loop.

3. The system as claimed in claim 2, wherein the optical monitor comprises a transmission window coupled to the recirculation loop and a reception window coupled to the recirculation loop, the windows having operating pressures above 3000 psi.

4. The system as claimed in claim 3, wherein a light source is coupled to the transmission window and a light detector is coupled to the reception window.

5. The system as claimed in claim 4, wherein the light source is an infrared light source and the light detector is an infrared light detector.

6. The system as claimed in claim 3, wherein the transmission window and the reception window are substantially transparent to infrared light.

7. The system as claimed in claim 3, wherein the transmission window and the reception window comprises calcium fluoride.

8. The system as claimed in claim 3, wherein the transmission window and the reception window are formed using an annular ring though which the processing fluid flows and comprises material that is substantially transparent to infrared light.

9. The system as claimed in claim 8, the monitoring system further comprising a holder coupled to the annular ring, the holder having an input port and an output port though which the processing fluid flows.

10. The system as claimed in claim 9, wherein the recirculation loop includes a first fluid line having a first end and a second fluid line having a second end, the holder comprising a first collar for coupling the input port to the first end and a second collar for coupling the output port to the second end.

11. The system as claimed in claim 10, wherein the first collar is coupled to a first surface of the annular ring, and the second collar is coupled to a second surface of the annular ring.

12. The system as claimed in claim 11, the monitoring system further comprising at least one clamp for securing the first collar to the second collar.

13. The system as claimed in claim 11, the monitoring system further comprising a first o-ring seal to seal the first collar to the first surface of the annular ring, and a second o-ring seal to seal the second collar to the second surface of the annular ring.

14. The system as claimed in claim 11, the monitoring system further comprising at least one coupling element for securing the first collar to the first fluid line, and at least one coupling element for securing the second collar to the second fluid line.

15. The system as claimed in claim 11, wherein a hole diameter in the annular ring is approximately equal to an inner diameter of the first fluid line.

16. The system as claimed in claim 15, wherein the inner diameter of the first fluid line is approximately equal to an inner diameter of the second fluid line.

17. The system as claimed in claim 9, wherein the holder comprises means for coupling an optical source and an optical detector to the annular ring for monitoring the flow of processing fluid therethrough.

18. The system as claimed in claim 1, wherein the controller determines the chemical composition using a Fourier Transform.

19. The system as claimed in claim 1, the monitoring system further comprising a temperature sensor, a pressure sensor, or a flow sensor, or a combination thereof.

20. The system as claimed in claim 1, wherein the fluid comprises gaseous, liquid, supercritical, or near-supercritical carbon dioxide, or a combination of two or more thereof.

21. The system as claimed in claim 1, wherein the process chemistry comprises a cleaning agent, a rinsing agent, a curing agent, a drying agent, or an etching agent, or a combination of two or more thereof.

22. The system as claimed in claim 1, the monitoring system further comprising a block of calcium fluoride including a hole through a thickness of the block through which the processing fluid passes.

23. A system for monitoring a processing fluid within a high-pressure processing system, the system comprising:

a recirculation loop comprising a high pressure processing chamber and a high pressure recirculation system coupled to the high pressure processing chamber, wherein the processing fluid flows through the recirculation loop;

a high-pressure fluid supply system coupled to the recirculation loop and comprising means for supplying fluid to the recirculation loop;

a process chemistry supply system coupled to the recirculation loop and comprising means for supplying process chemistry to the recirculation loop;

a pressure control system coupled to the recirculation loop;

an exhaust system coupled to the recirculation loop;

a monitoring system coupled to the recirculation loop before the high-pressure processing system for monitoring the processing fluid flowing directly into the high-pressure processing chamber; and a controller coupled to the high pressure processing chamber, the recirculation system, the high-pressure fluid supply system, the process chemistry supply system, the pressure control system, the exhaust system, and the monitoring system wherein the controller comprises means for determining a chemical composition of the processing fluid using data from the monitoring system, means for comparing the chemical composition to a threshold value, means for providing additional fluid to the recirculation loop when the chemical composition is greater than or equal to the threshold value, and means for providing additional process chemistry to the recirculation loop when the chemical composition is less than the threshold value.

* * * * *